US011865321B2

(12) United States Patent
Modi

(10) Patent No.: US 11,865,321 B2
(45) Date of Patent: Jan. 9, 2024

(54) FLUID DELIVERY DEVICE

(71) Applicant: PKA SOFTTOUCH CORP., Lakefield (CA)

(72) Inventor: Pankaj Modi, Ancaster (CA)

( * ) Notice: Subject to any disclaimer, the term of this patent is extended or adjusted under 35 U.S.C. 154(b) by 76 days.

(21) Appl. No.: 17/410,516

(22) Filed: Aug. 24, 2021

(65) Prior Publication Data

US 2021/0379295 A1 Dec. 9, 2021

Related U.S. Application Data

(63) Continuation of application No. 16/469,808, filed as application No. PCT/CA2017/051298 on Nov. 1, 2017, now abandoned.

(60) Provisional application No. 62/462,497, filed on Feb. 23, 2017, provisional application No. 62/434,760, filed on Dec. 15, 2016.

(51) Int. Cl.
*A61M 5/32* (2006.01)
*A61M 5/315* (2006.01)
*A61M 5/50* (2006.01)

(52) U.S. Cl.
CPC ...... *A61M 5/3271* (2013.01); *A61M 5/31501* (2013.01); *A61M 5/326* (2013.01); *A61M 5/50* (2013.01); *A61M 5/3202* (2013.01); *A61M 2005/3267* (2013.01)

(58) Field of Classification Search
CPC .. A61M 5/326; A61M 5/3271; A61M 5/3272; A61M 2005/3263; A61M 2005/3267
See application file for complete search history.

(56) References Cited

U.S. PATENT DOCUMENTS

| 2,371,086 A | 3/1945 | Edward et al. |
| 3,527,215 A | 9/1970 | De Witt et al. |
| 4,883,473 A | 11/1989 | Thomas |
| 4,886,499 A | 12/1989 | Cirelli et al. |
| 4,955,871 A | 9/1990 | Thomas |
| 5,527,288 A | 6/1996 | Gross et al. |

(Continued)

FOREIGN PATENT DOCUMENTS

| CA | 2126320 | 1/1993 |
| CA | 2376147 | 1/2001 |

(Continued)

OTHER PUBLICATIONS

OA JP2019-553604, Jul. 2, 2021, PKA Softtouch Corp.

(Continued)

*Primary Examiner* — Laura A Bouchelle

(57) ABSTRACT

Disclosed herein is a fluid dispenser comprising a barrel defining a longitudinal axis terminating at a first fluid delivery end region; a body movable along the barrel relative to the first fluid delivery end region, the body including a needle carrier, a plunger and a capsule carrier therebetween, a latch interface between the body and the barrel and responsive to a release force therebetween caused by compressive engagement of the barrel at a fluid delivery site on a patient, to enable travel of the plunger and capsule carrier toward the needle carrier, to a dispensing configuration in which an upstream end of the needle pierces the capsule and projects form the first fluid delivery end region to deliver a fluid to the fluid delivery site.

12 Claims, 16 Drawing Sheets

(56) References Cited

U.S. PATENT DOCUMENTS

| | | |
|---|---|---|
| 5,658,259 A | 9/1997 | Pearson et al. |
| 5,931,814 A | 8/1999 | Alex et al. |
| 5,964,736 A | 10/1999 | Lane |
| 5,997,501 A | 12/1999 | Gross et al. |
| 6,099,504 A | 8/2000 | Gross et al. |
| 6,102,896 A | 8/2000 | Roser |
| 6,387,078 B1 | 5/2002 | Gillespie, III et al. |
| 6,494,865 B1 | 12/2002 | Alchas et al. |
| 6,569,143 B2 | 5/2003 | Alchas et al. |
| 6,607,509 B2 | 8/2003 | Bobroff et al. |
| 6,620,134 B1 | 9/2003 | Trombley et al. |
| 6,689,118 B2 | 1/2004 | Alchas et al. |
| 6,808,507 B2 | 10/2004 | Roser |
| 6,896,666 B2 | 5/2005 | Kochamba |
| 6,979,316 B1 | 12/2005 | Rubin et al. |
| 2005/0124967 A1 | 6/2005 | Kaestner et al. |
| 2006/0229562 A1 | 10/2006 | March et al. |
| 2007/0265568 A1 | 11/2007 | Tsals |
| 2012/0041379 A1 | 2/2012 | Macarthur et al. |
| 2012/0245558 A1 | 9/2012 | Durack |
| 2013/0245561 A1* | 9/2013 | Kouyoumjian ... A61M 5/31596 604/191 |
| 2014/0207078 A1 | 7/2014 | Modi |
| 2014/0288504 A1 | 9/2014 | Karlsson |
| 2014/0303556 A1 | 10/2014 | Travanty |

FOREIGN PATENT DOCUMENTS

| | | |
|---|---|---|
| CA | 2536845 | 2/2006 |
| EP | 20330785 | 9/1989 |
| EP | 0652027 A1 | 5/1995 |
| EP | 1452196 | 9/2004 |
| EP | 2875838 A1 | 5/2015 |
| EP | 2918301 | 9/2015 |
| WO | WO9954217 A1 | 10/1999 |
| WO | WO 03/037410 A1 | 5/2003 |
| WO | WO2006129196 A1 | 12/2006 |
| WO | WO2011039206 | 4/2011 |
| WO | WO2014013594 A1 | 1/2014 |

OTHER PUBLICATIONS

OA BR112019011768-7, Feb. 22, 2022, PKA Softtouch Corp.
ISR PCT/CA2017/051298, Mar. 1, 2018, PKA Softtouch Corp.
IPRP PCT/CA2017/051298, Jun. 27, 2019, PKA-Softtouch Corp.
ISR PCT/CA2007/000225, May 18, 2007, PKA Softtouch Corp.
EP 07701776.2-1257, Aug. 23, 2007, PKA Softtouch Corp.
IPRP PCT/CA2007/000225, Aug. 19, 2009, PKA Softtouch Corp.

* cited by examiner

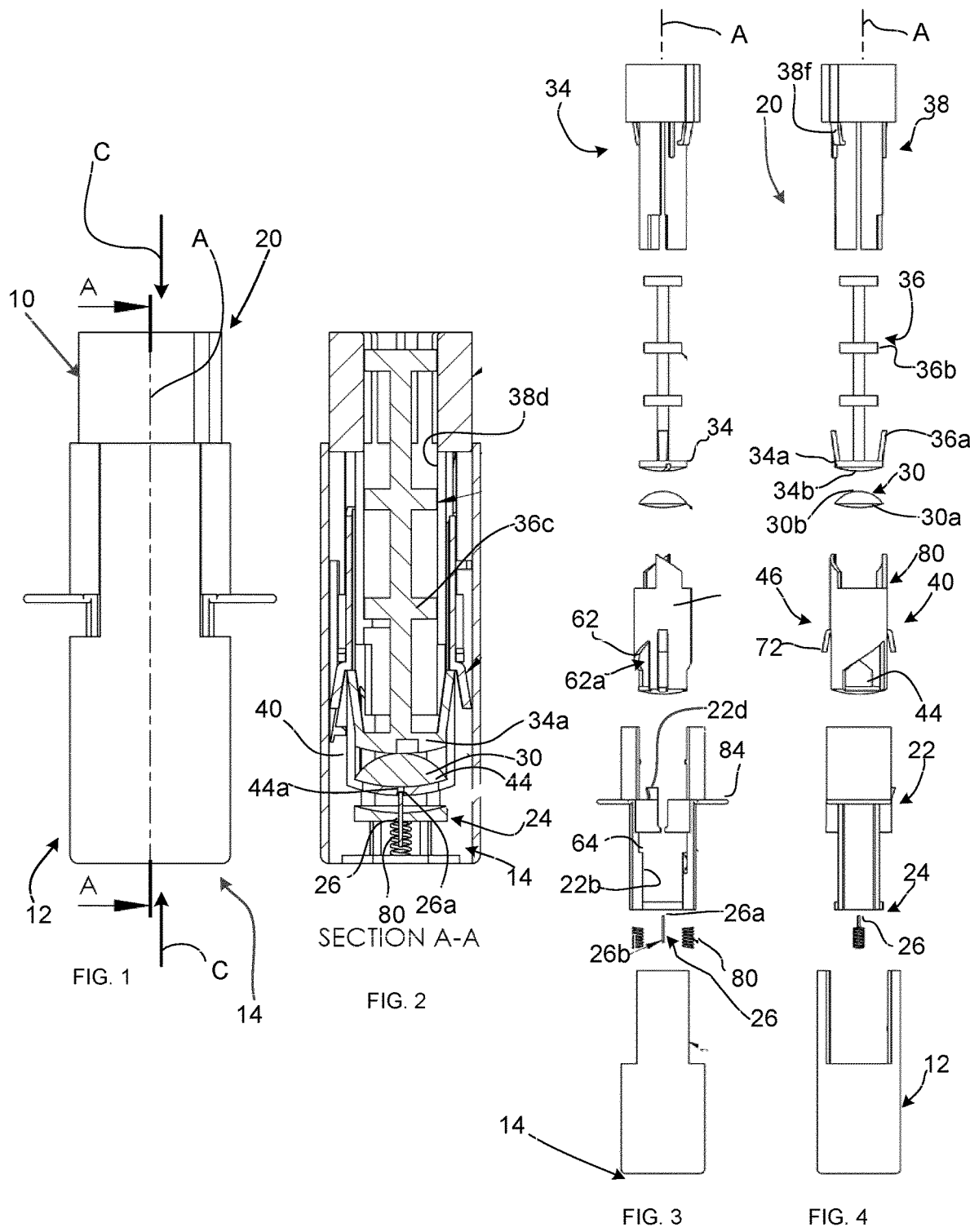

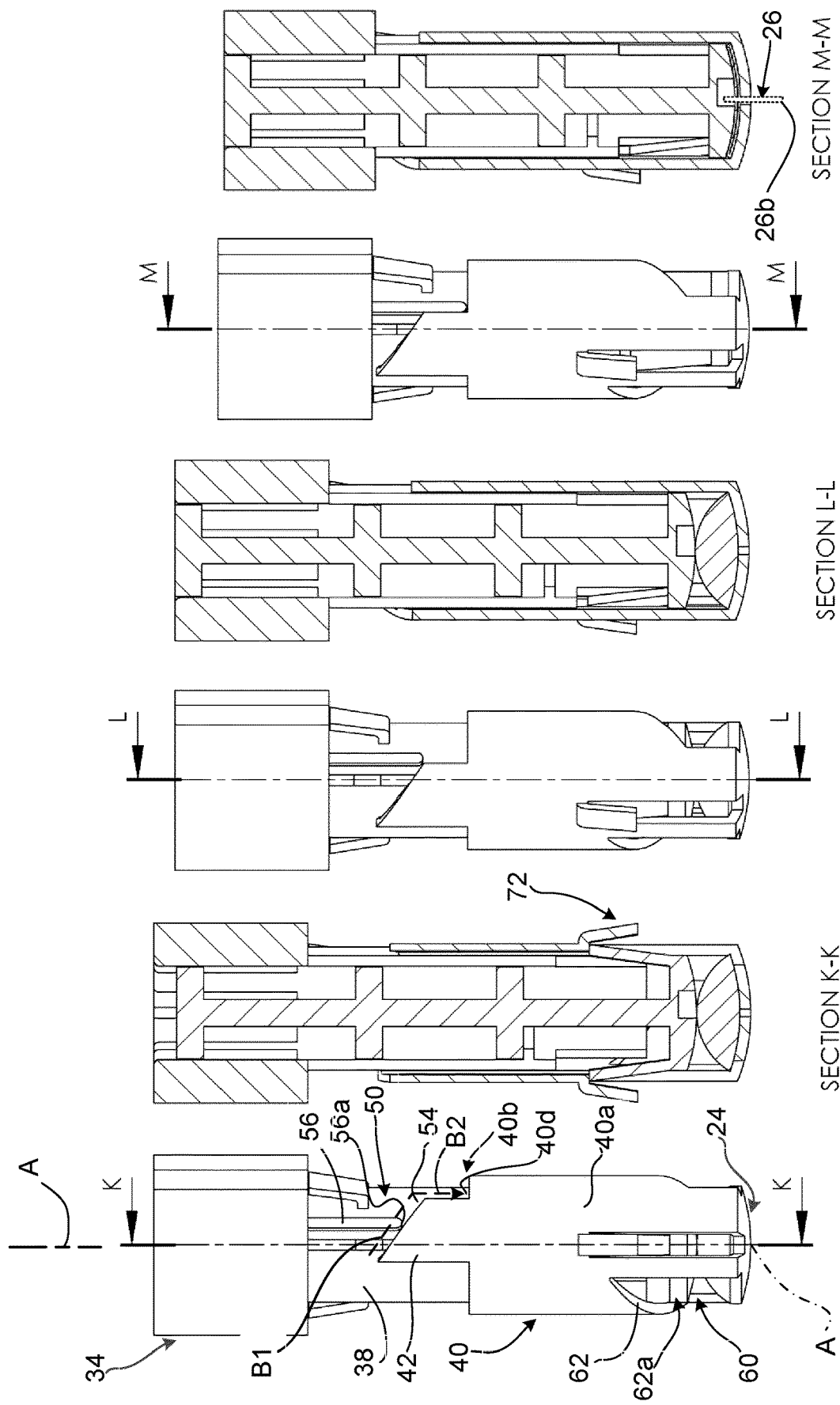

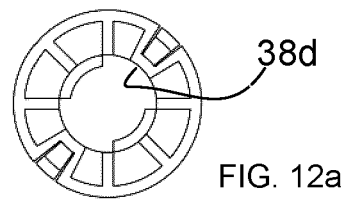
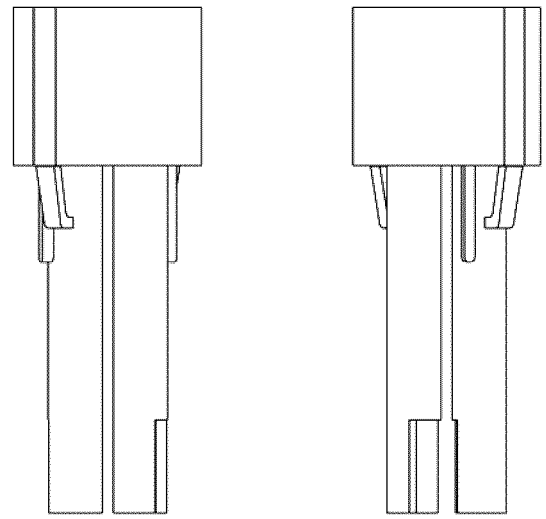
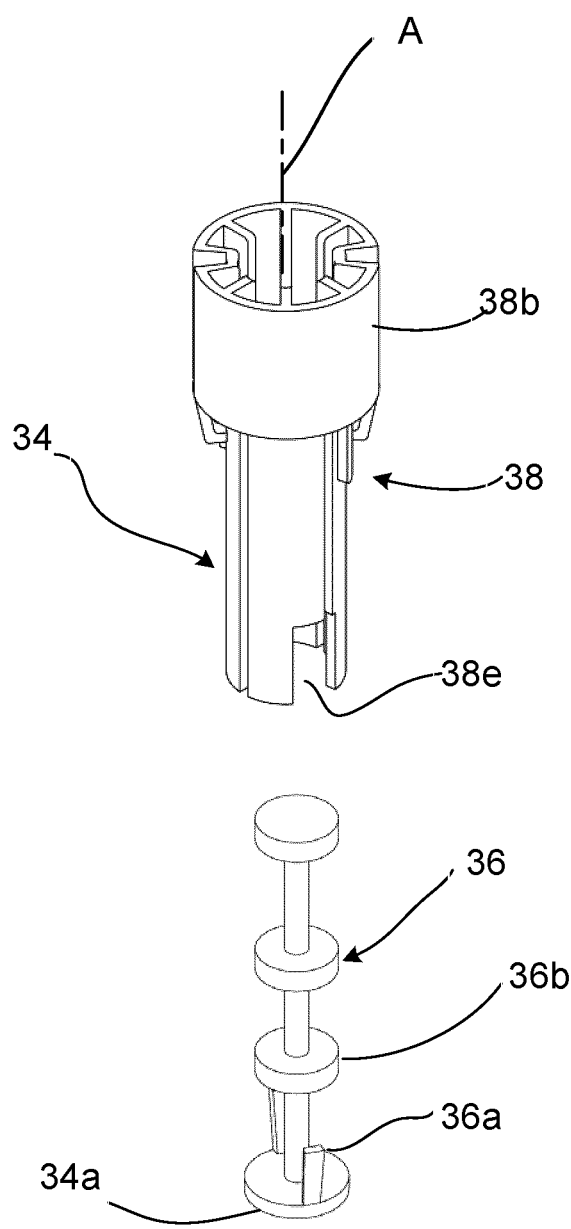
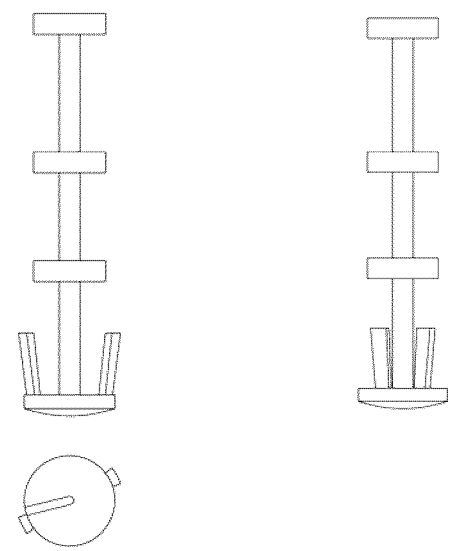
FIG. 12a
FIG. 13
FIG. 11  FIG. 12

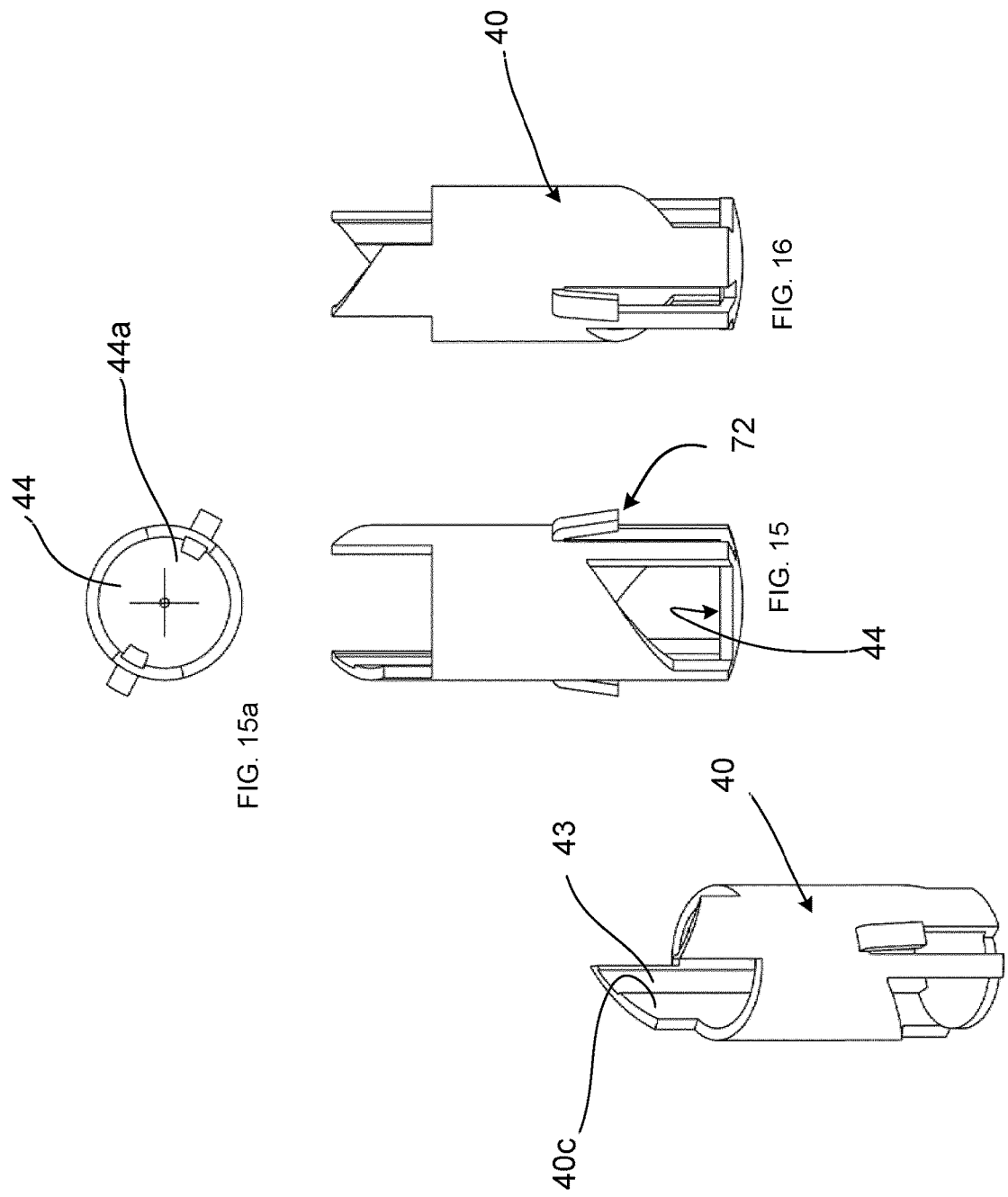

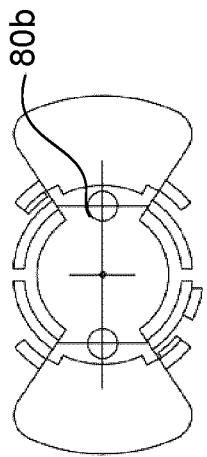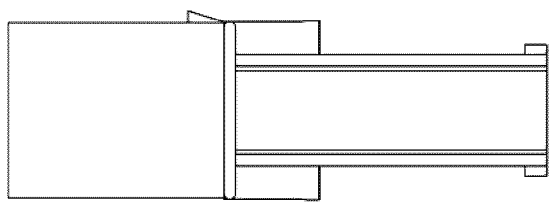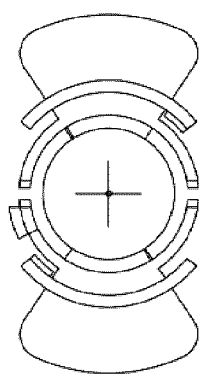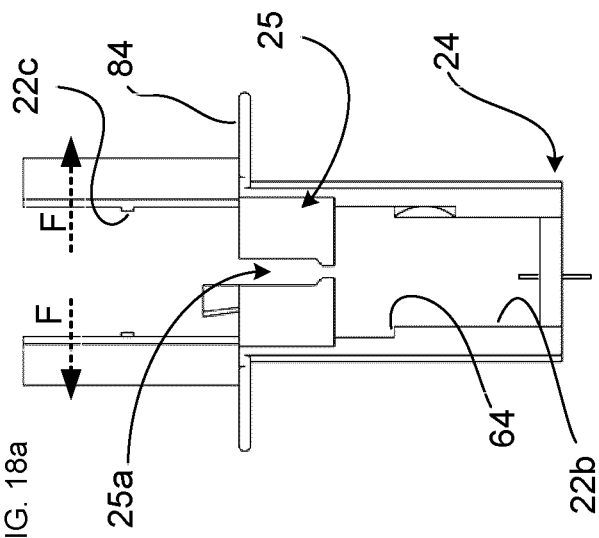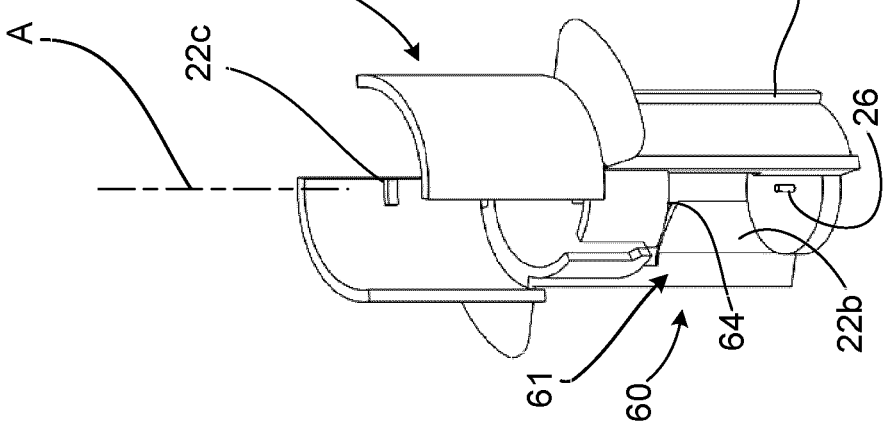

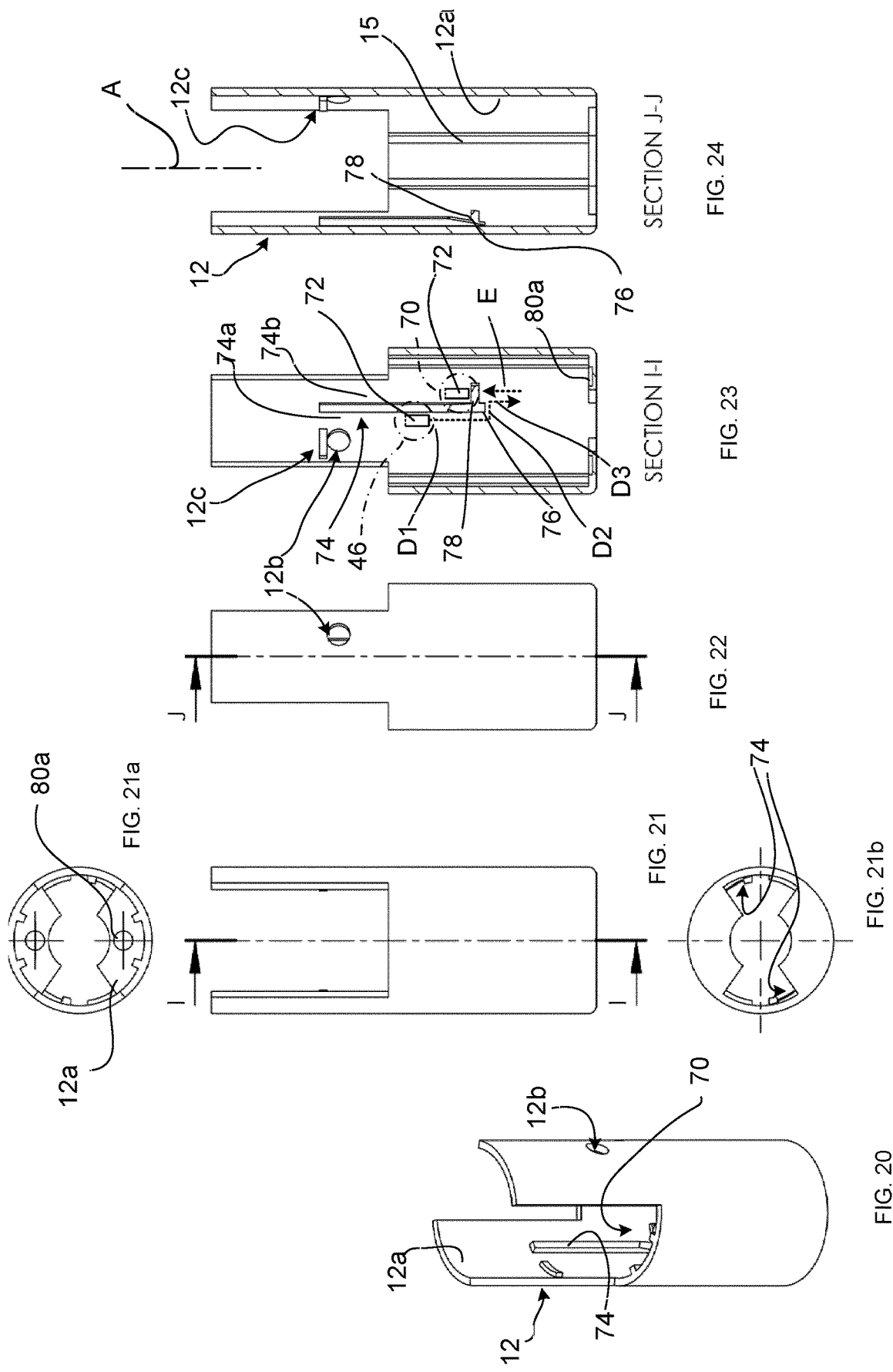

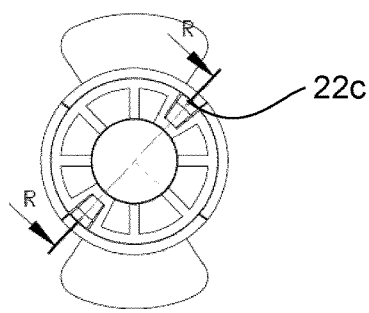
FIG. 32
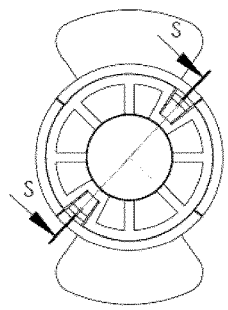
FIG. 33
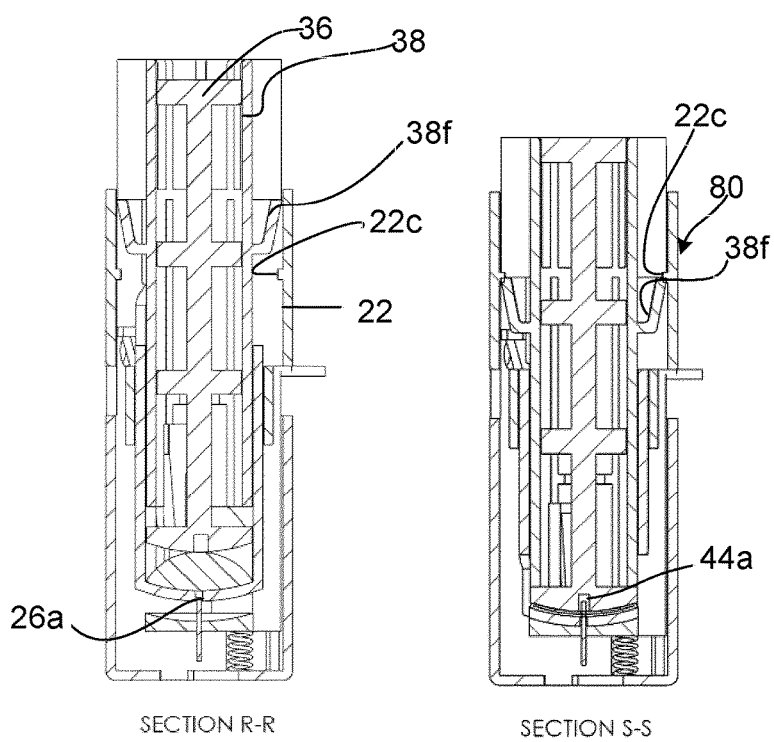
SECTION R-R
FIG. 34
SECTION S-S
FIG. 35

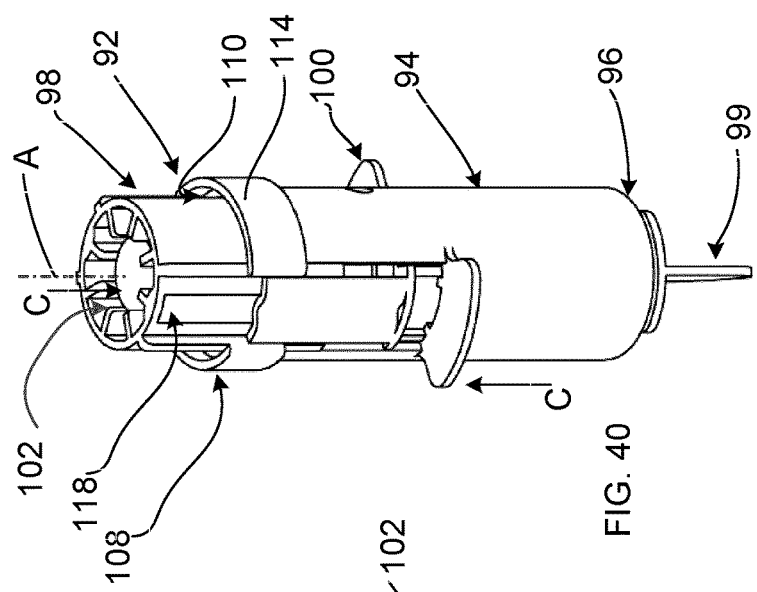
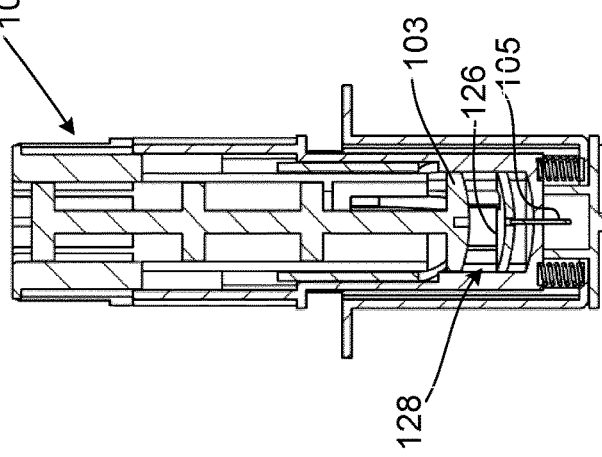
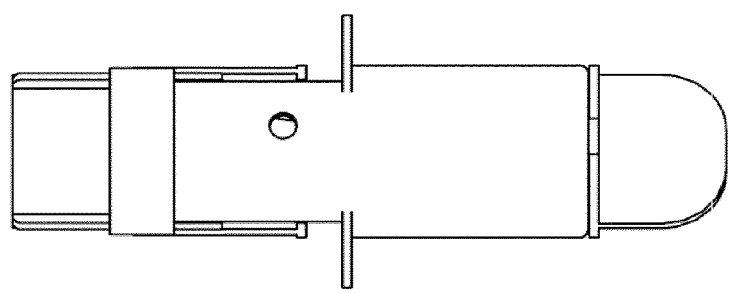
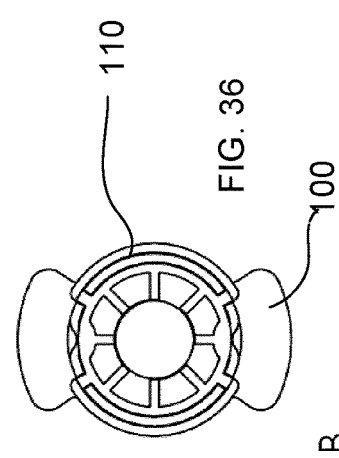
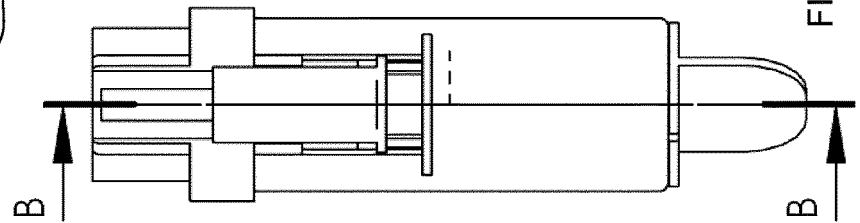

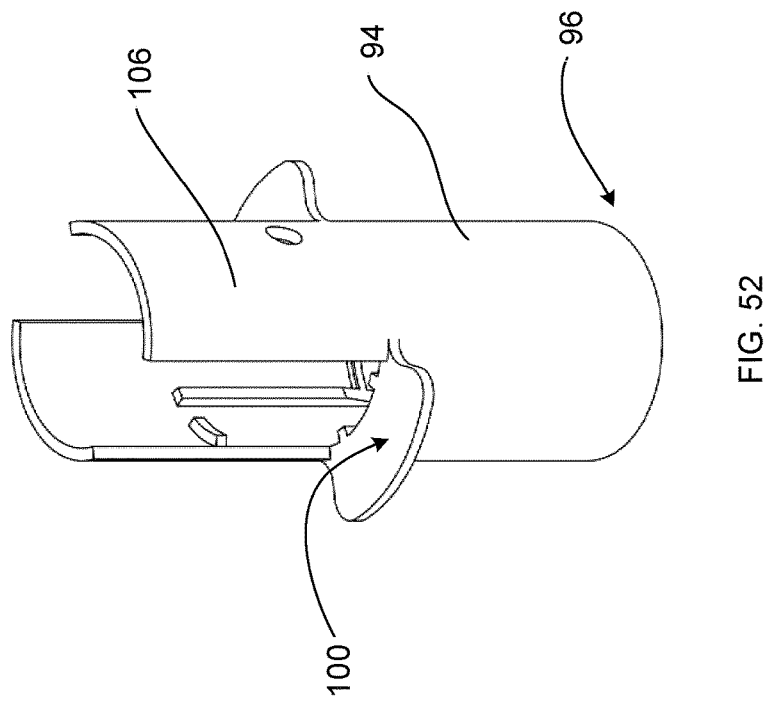
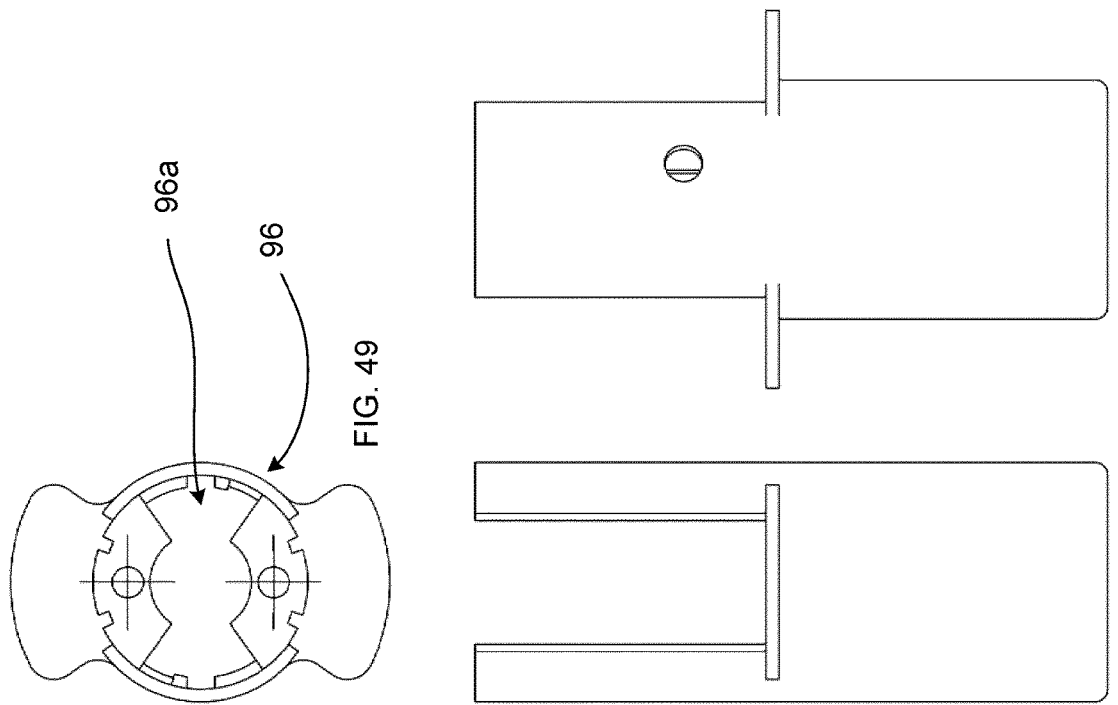
FIG. 52
FIG. 51
FIG. 49
FIG. 50

FLUID DELIVERY DEVICE

REFERENCE TO COPENDING APPLICATIONS

The entire subject matter, including materials submitted at filing, of each of:
U.S. Non-Provisional application Ser. No. 15/361,654, filed Nov. 28, 2016 entitled DRUG DELIVERY DEVICE;
U.S. Provisional application 62/434,760, filed Dec. 15, 2016 entitled DRUG DELIVERY DEVICE; and
U.S. Provisional application 62/462,497, filed Feb. 23, 2017 entitled DRUG DELIVERY DEVICE;
is fully incorporated herein by reference.

FIELD

The present disclosure relates to fluid delivery devices and methods, for example intradermal drug delivery devices and methods.

BACKGROUND

There is a well-established need to improve drug delivery techniques, to reduce discomfort, while improving ease of handling and safety for medical professionals. The above mentioned application Ser. No. 14/562,974, published as US 2014-0207078-A1 discloses a number of approaches to address this need.

The present disclosure aims to provide further novel approaches to overcome at least some drawbacks of known techniques, or at least that provides one or more useful alternatives.

SUMMARY

The following presents a simplified summary of the general inventive concept herein to provide a basic understanding of some aspects of the invention. This summary is not an extensive overview of the invention. It is not intended to restrict key or critical elements of the invention or to delineate the scope of the invention. Furthermore, any one element, feature, structure, function, of any aspect and/or exemplary embodiment described in the present disclosure including the figures, clauses and/or claims herein, may be combined with any one or more elements, features, structures, functions, and/or steps from the same or any other aspects and/or exemplary embodiments described in the present disclosure including the figures, clauses and/and claims herein.

In an aspect, there is provided a fluid dispenser comprising a barrel defining a longitudinal axis terminating at a first fluid delivery end region; a dispenser body movable along the barrel relative to the first fluid delivery end region in a first phase between a pre-dispensing configuration and a dispensed configuration, and in a second phase between the dispensed configuration and a locked post-dispensing configuration, wherein the dispenser body is configured to rotate about the longitudinal axis during the first phase for aligned orientation with at least one locking structure configured to lock the dispenser body in the locked post-dispensing configuration during travel in the second phase.

In another aspect, there is provided a fluid dispenser comprising:
a. a barrel defining a longitudinal axis terminating at a first fluid delivery end region;
b. a body movable along the barrel relative to the first fluid dispensing end region, the body including:
   i. a needle carrier aligned with the longitudinal axis and terminating at a second fluid delivery end region, at which is located a needle having a downstream end configured to project through the first fluid delivery end region in a first dispensing position;
   ii. a plunger structure aligned with the longitudinal axis and movable axially relative to the needle carrier; and
   iii. a fluid capsule carrier which is configured to receive a fluid capsule, the fluid capsule carrier being aligned with the longitudinal axis and movable axially relative to the needle carrier and the plunger structure;
   iv. a latch interface operable under the action of a compressive force between the barrel and the body, to release the plunger structure to travel relative to the needle carrier; and
   v. the fluid capsule carrier configured, in a dispensing mode, to travel toward piercing contact of the needle with the fluid capsule.

In another aspect, there is provided a fluid dispenser comprising a barrel defining a longitudinal axis and terminating at a first fluid delivery end region; a body movable along the barrel relative to the first fluid delivery end region, the body including a needle carrier, a plunger and a fluid capsule carrier therebetween, a latch interface between the body and the barrel and responsive to a release force therebetween caused by compressive engagement of the barrel at a fluid delivery site, to enable travel of the plunger and the fluid capsule carrier toward the needle carrier, to a dispensing configuration in which an upstream end of a needle on the needle carrier extends into a capsule carrying region of the fluid capsule carrier and a downstream end of the needle projects extends through the first fluid delivery end region for delivery of a fluid thereto.

In another aspect, there is provided a fluid dispenser comprising a barrel defining a longitudinal axis terminating at a dispensing end; a dispenser body movable along the barrel relative to the dispensing end, the dispenser body including a needle carrier, a plunger and a fluid capsule carrier moveable relative to the needle carrier and the plunger, and a latch interface configured to release the dispenser body for travel in the barrel in response to a release force between the barrel and the dispenser body.

In another aspect, there is provided a fluid dispenser comprising a barrel defining a longitudinal axis terminating at a dispensing end; a dispenser body movable along the barrel relative to the dispensing end, the dispenser body including a needle carrier, a plunger and a fluid capsule carrier moveable relative to the needle carrier and the plunger, and a latch interface configured to release the dispenser body for dispensing travel in the barrel in response to a compressive engagement of the dispensing end at a fluid delivery site.

In another aspect, there is provided a fluid dispenser, comprising a fluid capsule receiver configured to form a fluid capsule pressuring zone in a first capsule pressurizing mode, a needle carrier supporting a fluid delivery needle, the needle carrier and the fluid capsule receiver configured to cause the needle to extend into the fluid capsule pressurizing zone to pierce the pressurized fluid capsule in a second fluid capsule piercing mode; and a body containing the fluid capsule receiver and the needle carrier, the fluid capsule receiver and the needle carrier configured to move along the body to expose a fluid delivery end of the needle in a third fluid delivery mode.

In another aspect, there is provided a method of dispensing a fluid from a fluid capsule, comprising:
  locating a fluid capsule on a fluid capsule support surface;
  displacing a plunger along an axis to toward engagement with the fluid capsule;
  pressurizing the fluid capsule between the plunger and the fluid capsule support surface, so that a membrane of the fluid capsule against the fluid capsule support surface is in a tensioned needle receiving configuration;
  displacing the plunger and the fluid capsule support, with the fluid capsule in the needle receiving configuration toward a needle support to cause a capsule-piercing end of a fluid delivery needle thereon, to extend through the fluid capsule support surface to penetrate the membrane to initiate onset of dispensing of fluid through the needle; and
  advancing the plunger, the fluid capsule support and the needle support toward a fluid delivery configuration with an opposite fluid delivery end of the needle exposed to penetrate a delivery location.

In another aspect, there is provided a method of securing a dispensing device following delivery of a fluid therefrom, comprising providing a barrel defining a longitudinal axis terminating at a first fluid delivery end region and a dispenser body movable along the barrel relative to the first fluid delivery end region, the dispenser body movable in a first phase between a pre-dispensing configuration and a dispensed configuration, and in a second phase between the dispensed configuration and a locked post-dispensing configuration, wherein the dispenser body is configured to rotate about the longitudinal axis, at least in part, during the first phase for aligned orientation with at least one locking structure during travel in the second phase.

In another aspect, there is provided a method of securing a dispensing device following delivery of a fluid therefrom, comprising:
  providing a barrel defining a longitudinal axis terminating at a first fluid delivery end region and a dispenser body movable along the barrel relative to the first fluid delivery end region;
  displacing the dispenser body in a first phase between a pre-dispensing configuration and a dispensed configuration, and in a second phase between the dispensed configuration and a locked post-dispensing configuration, wherein the dispenser body is rotated about the longitudinal axis, at least in part, during the first phase and/or the second phase for aligned orientation with at least one locking structure during travel in the second phase.

In another aspect, there is provided a fluid dispenser comprising a barrel defining a longitudinal axis terminating at a first fluid delivery end region; a dispenser body movable along the barrel relative to the first fluid delivery end region in a first phase between a pre-dispensing configuration and a dispensed configuration, and in a second phase between the dispensed configuration and a locked post-dispensing configuration, wherein the dispenser body is configured to rotate about the longitudinal axis during the first phase and/or the second phase for aligned orientation with at least one locking structure configured to lock the dispenser body in the locked post-dispensing configuration during travel in the second phase.

In another aspect, there is provided a fluid dispenser comprising housing means defining a longitudinal axis terminating at a first fluid delivery end region; dispensing means movable along the housing means relative to the first fluid delivery end region in a first phase between a pre-dispensing configuration and a dispensed configuration, and in a second phase between the dispensed configuration and a locked post-dispensing configuration, wherein the dispensing means is configured to rotate about the longitudinal axis during the first phase and/or the second phase for aligned orientation with at least one locking means during travel in the second phase.

In another aspect, there is provided a fluid dispenser comprising housing means defining a longitudinal axis terminating at a first fluid delivery end region; dispensing means movable along the housing means relative to the first fluid delivery end region in a first phase between a pre-dispensing configuration and a dispensed configuration, and in a second phase between the dispensed configuration and a locked post-dispensing configuration, wherein the dispensing means is configured to rotate about the longitudinal axis during the first phase for aligned orientation with at least one locking means during travel in the second phase.

BRIEF DESCRIPTION OF THE DRAWINGS

Several exemplary embodiments will be provided, by way of examples only, with reference to the appended drawings, wherein:
FIGS. 1, 2 and 3 to 4 are, respectively, side, sectional and assembly views of a dispenser;
FIGS. 5 to 10 are side or sectional views of the dispenser of FIG. 1 in different configurations;
FIGS. 11 to 13 are perspective or side assembly views of structures of the dispenser of FIG. 1;
FIG. 12a is a top plan view of a structure shown in FIG. 12;
FIGS. 14 to 16 are perspective or side views of structures of the dispenser of FIG. 1;
FIG. 15a is a top plan view of a structure shown in FIG. 15;
FIGS. 17 to 19 are perspective or side views of a structure of the dispenser of FIG. 1;
FIGS. 18a and 19a are top plan views of the structure shown in FIGS. 18 and 19 respectively;
FIGS. 20 to 24 are perspective or side views of a structure of the dispenser of FIG. 1;
FIGS. 21a and 21b are top and bottom plan views, respectively, of the structure shown in FIG. 21;
FIGS. 32 to 35 are sectional views showing additional features of the dispenser of FIG. 1;
and
  FIGS. 36 to 56 are views showing another dispenser and/or structures thereof.

DESCRIPTION OF THE EXEMPLARY EMBODIMENTS

Figures 25, 26:
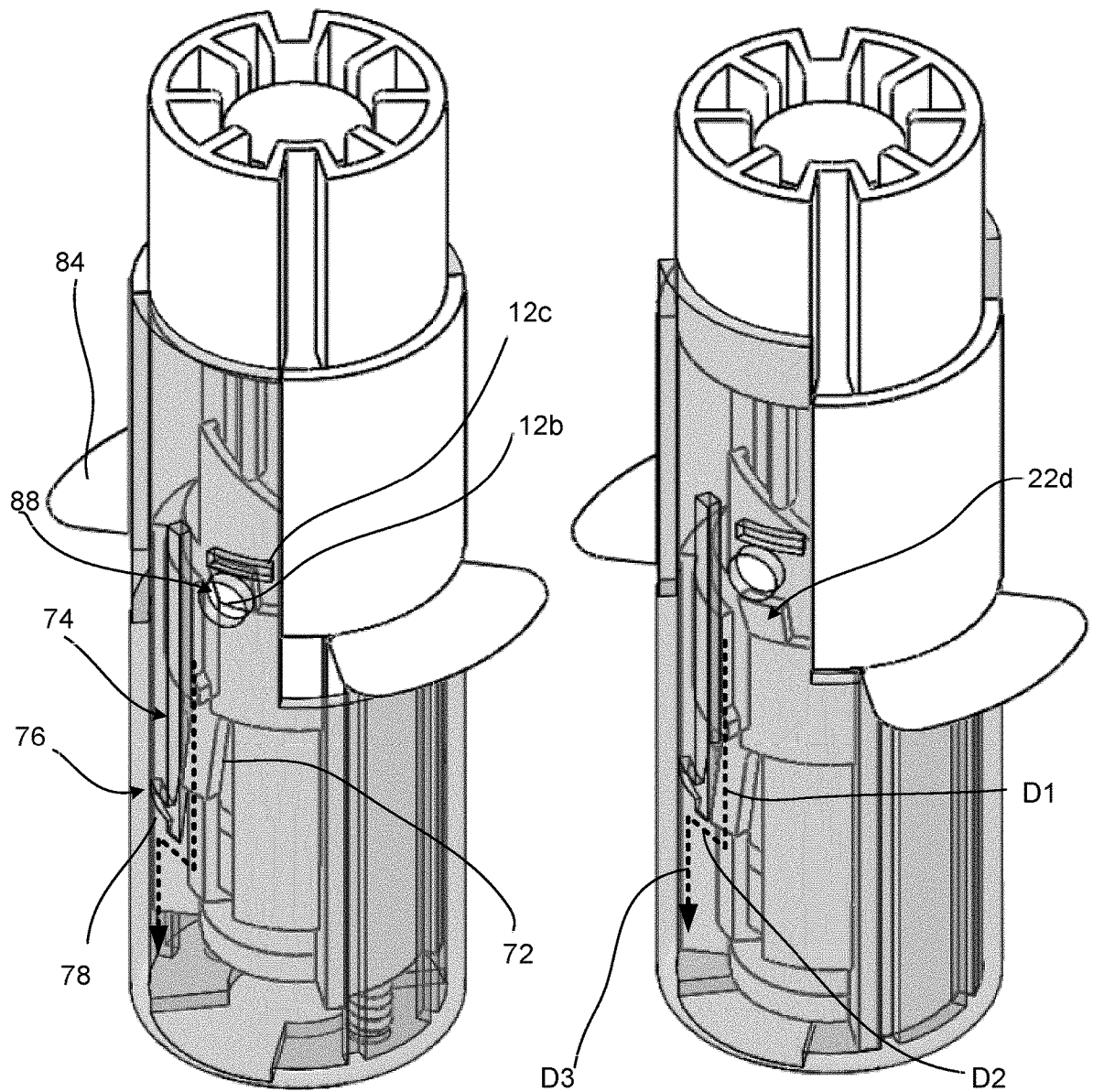
FIGS. 25 to 31 are perspective views of structures of the dispenser of FIG. 1.

It should be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Furthermore, and as described in subsequent paragraphs, the specific mechanical and/or other configurations illustrated in the drawings are intended to exemplify embodiments of the invention. However, other alternative mechanical and/or electrical or other configurations are possible which are considered to be within the teachings of the present disclosure.

Exemplary embodiments herein may be used to deliver a variety of active agents. The term "drug" is used loosely herein to refer to prophylactic as well as therapeutic agents. For example, vaccines may be delivered using the device. In addition, the term refers broadly to active agents, such as nucleic acids, small molecules, therapeutic proteins, hormones, analgesics, etc. in additional to traditional pharmacologic agents. Typical drugs include peptides, proteins or hormones such as insulin, calcitonin, calcitonin gene regulating protein, atrial natriuretic protein, colony stimulating factor, betaseton, erythropoietin (EPO), interferons such as α, β, or γ interferon, somatropin, somatotropin, somatostatin, insulin-like growth factor (somatomedins), luteinizing hormone releasing hormone (LHRH), tissue plasminogen activator (TPA), growth hormone release hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorephone, methadone, lidocaine, bupivacaine, diclofenac, naproxen, pavefin, and analogues thereof; anti-migraine agents such as sumatriptan, ergot alkaloids, and analogues thereof; anti-coagulant agents such as hepafin, hirudin, and analogues thereof; anti-emetic agents such as scopolamine, ondansetron, domperidone, metoclopramide, and analogues thereof; cardiovascular agents, anti-hypertensive agents and vasodilator such as diltiazem, clonidine, nifedipine, verapamil, isosorbide-5-mononitrate, organic nitrates, agents used in treatment of heart disorders, and analogues thereof; sedatives such as benzodiazepines, phenothiozines, and analogues thereof; narcotic antagonists such as naltrexone, naloxone, and analogues thereof; chelating agents such as deferoxamine, and analogues thereof; anti-diuretic agents such as desmopressin, vasopressin, and analogues thereof; antineoplastics such as 5-fluorouracil, bleomycin, and analogues thereof; prostaglandins and analogues thereof; and chemotherapy agents such as vincristine, and analogues thereof. Stabilized preparations of drugs that can be stored at room temperature are particularly preferred for use in the device and method.

The term "fluid" refers to any fluid containing, or not containing, a drug, an active agent or communication of drugs or agents, that can pass through the cannula of the microneedle. This includes a liquid, a solution, a gel, a dispersion or a fine suspension.

Referring to FIGS. 1 to 4, there is provided an exemplary embodiment of a dispenser 10 for dispensing a fluid such as one containing a drug. While the dispenser 10 may be deployed for non-drug-containing fluids, the following discussion is provided with respect to drug containing fluids.

The dispenser 10 comprises a barrel (or housing) 12, defining a longitudinal axis A terminating at a first fluid delivery end region 14. A body, generally shown at 20, is movable along the barrel 12 relative to the first fluid delivery end region 14. The body 20 includes a needle carrier 22 aligned with the longitudinal axis A and terminating at a second fluid delivery end region 24, at which is located a needle 26. The needle 26 has an upstream end 26a which is exposed inwardly to pierce a membrane 30a on a fluid capsule 30, and a downstream end 26b (as shown in dashed lines in FIG. 10) configured to project through the first fluid delivery end region 14 to deliver the fluid in a first dispensing position.

A plunger structure 34 is aligned with the longitudinal axis A and movable axially relative to the needle carrier 22, while a fluid capsule carrier 40 is aligned with the longitudinal axis A and movable axially relative to the needle carrier 22 and the plunger structure 34. As will be described, a latch interface (a portion of which is generally shown at 46 in FIG. 4) is operable under the action of a compressive force C (FIG. 1) acting against the barrel 12 and the body 20, to release the plunger structure 34, so that it can travel relative to the needle carrier 22.

The fluid capsule carrier 40 is configured, in a first phase (or dispensing mode) to travel toward piercing contact by the upstream end 26a of needle 26 with the membrane 30a. In some cases, the fluid capsule carrier 40 is configured to travel with the plunger structure 34, for at least part of the first phase.

Figure 27:
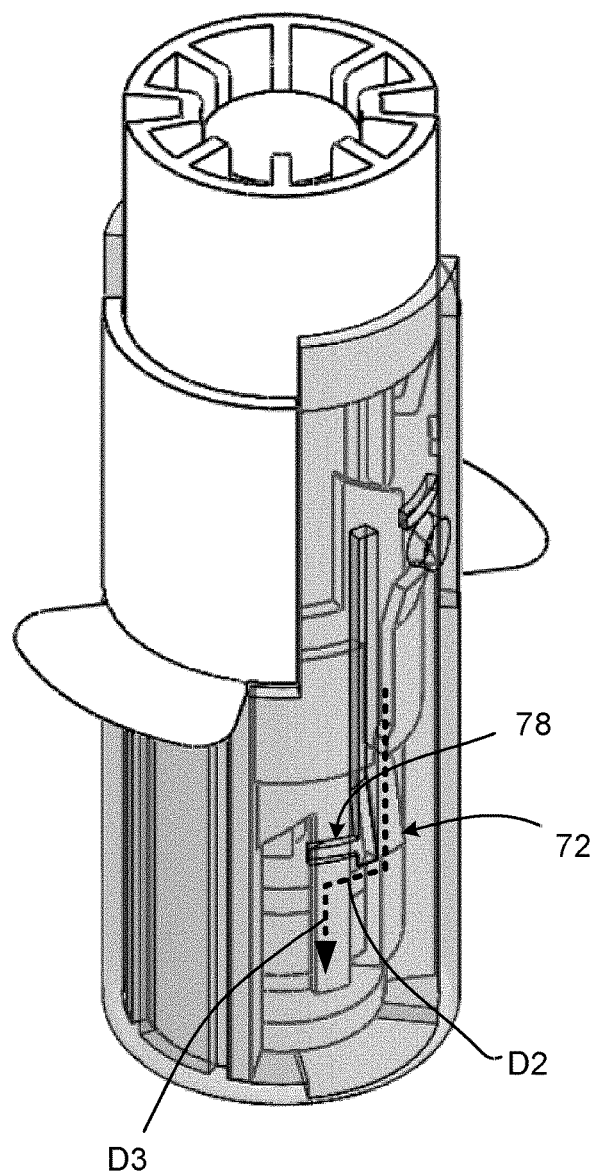
Figure 28:
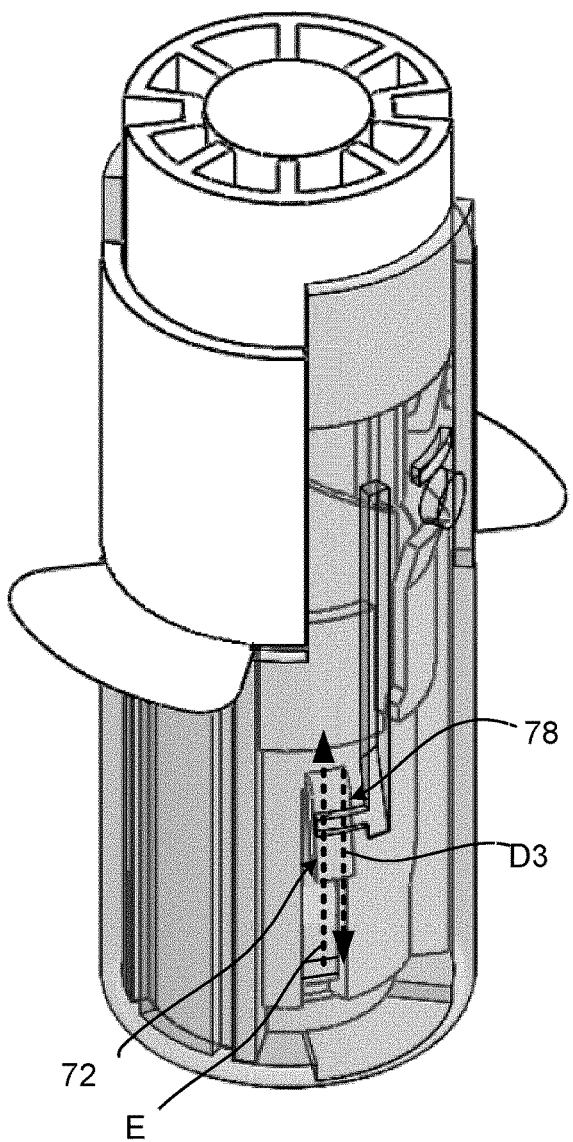
Figure 29:
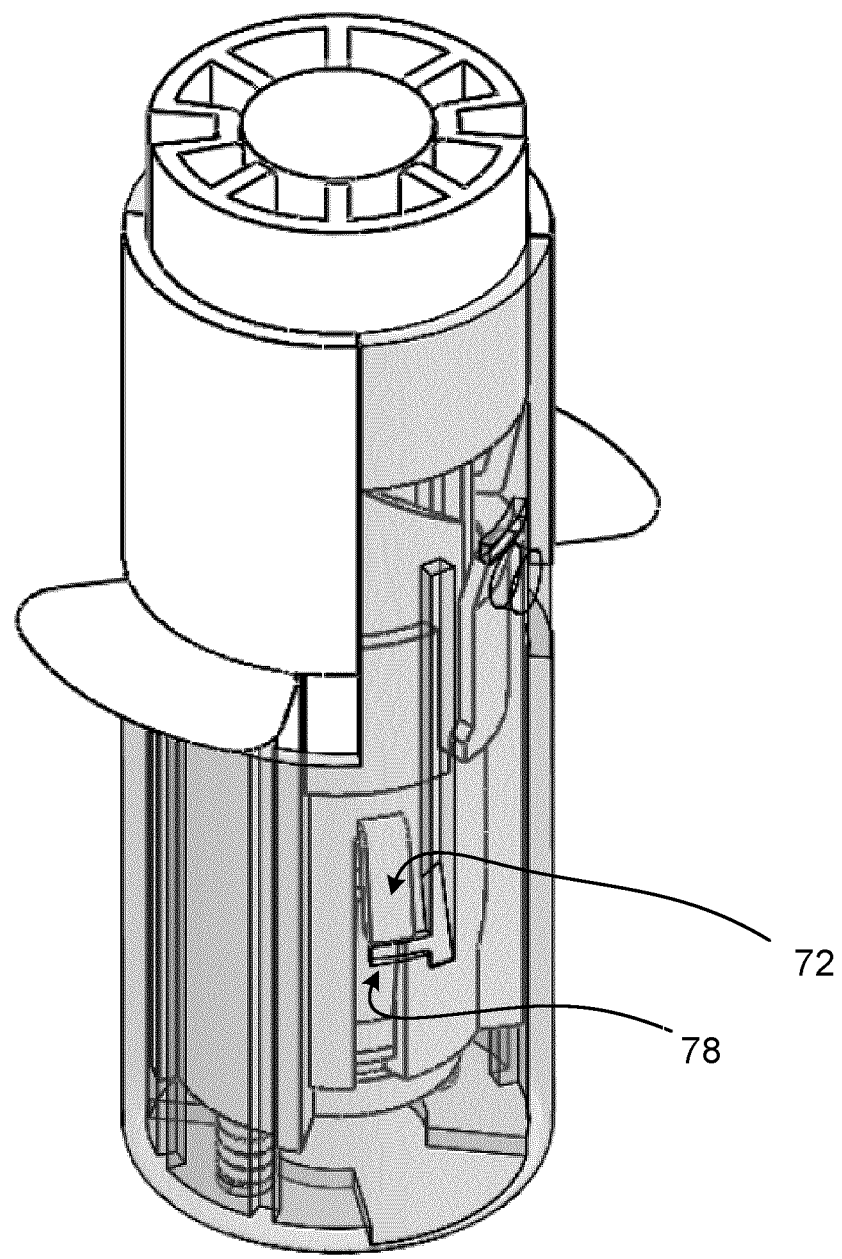
Figure 30:
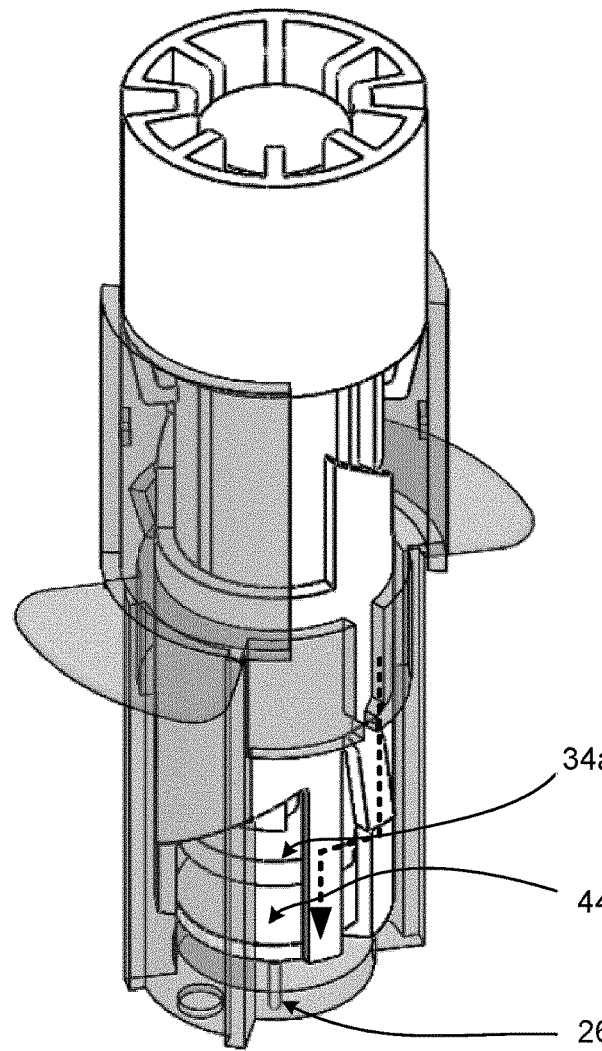
Figure 31:
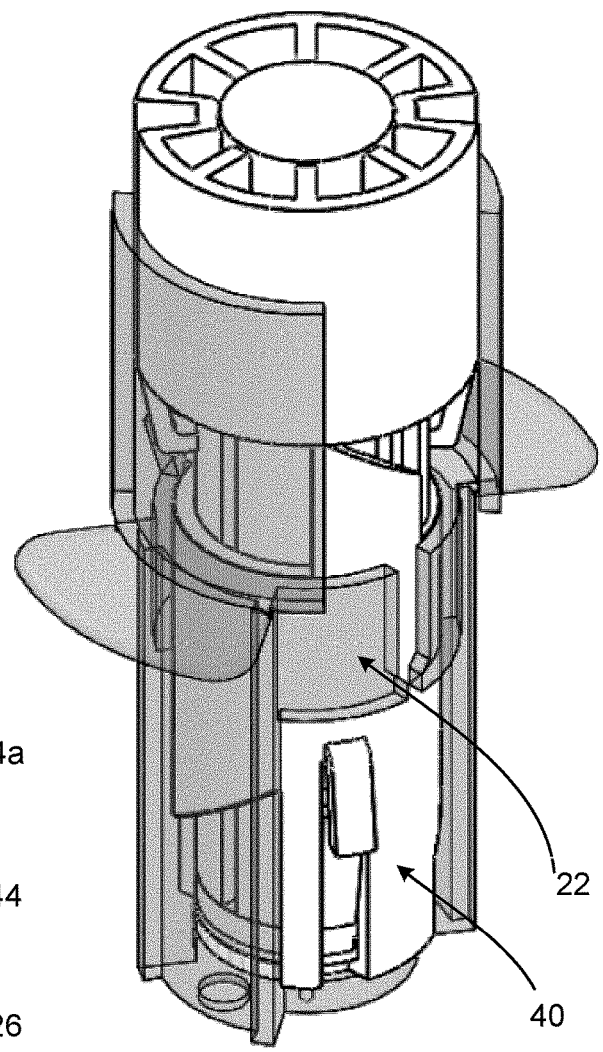
Figure 44:
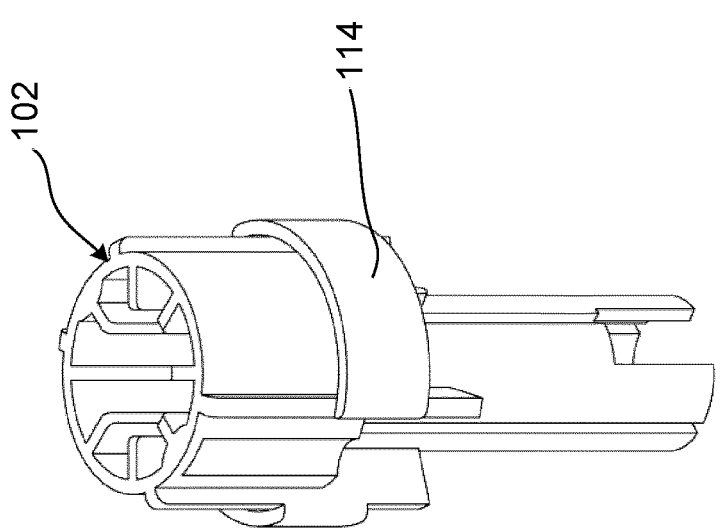
Figure 41:
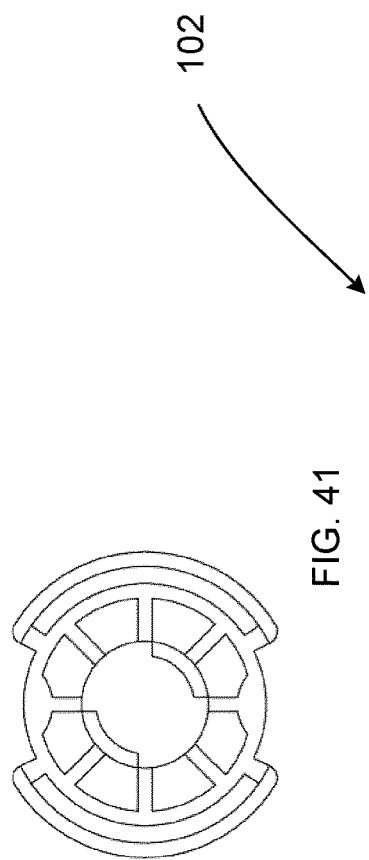
Figure 43:
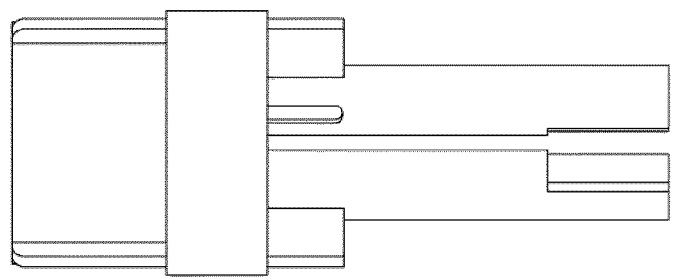
Figure 42:
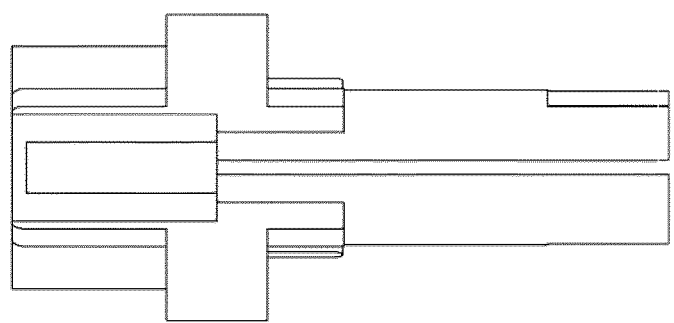
Figure 48:
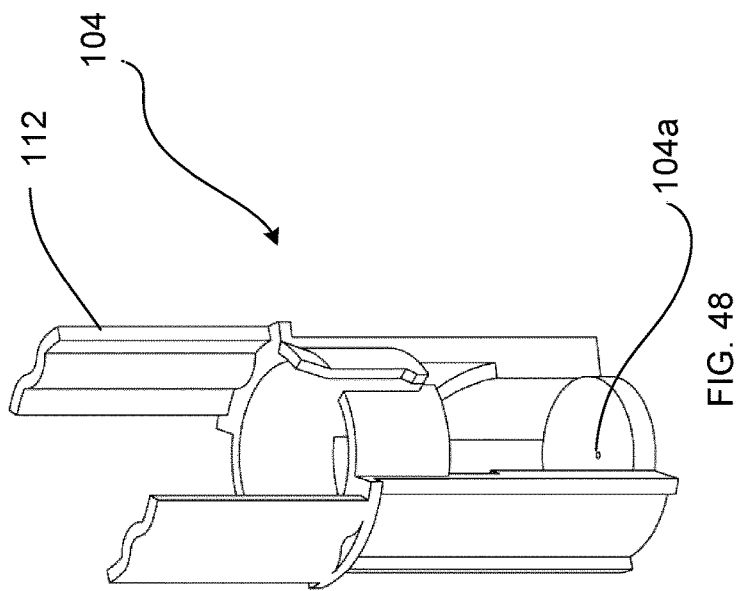
Figure 47:
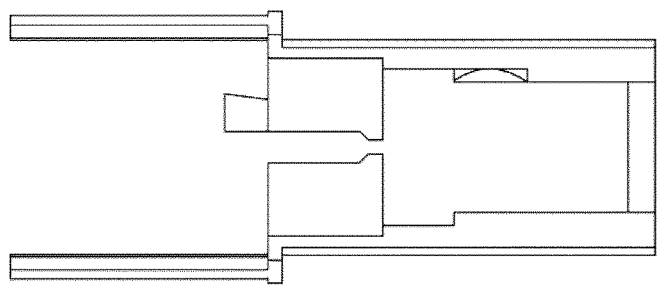
Figure 45:
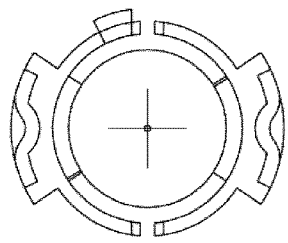
Figure 46:
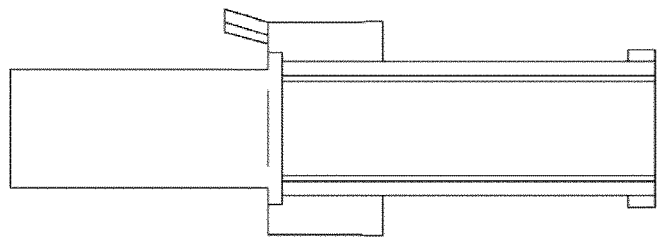
Figure 56:
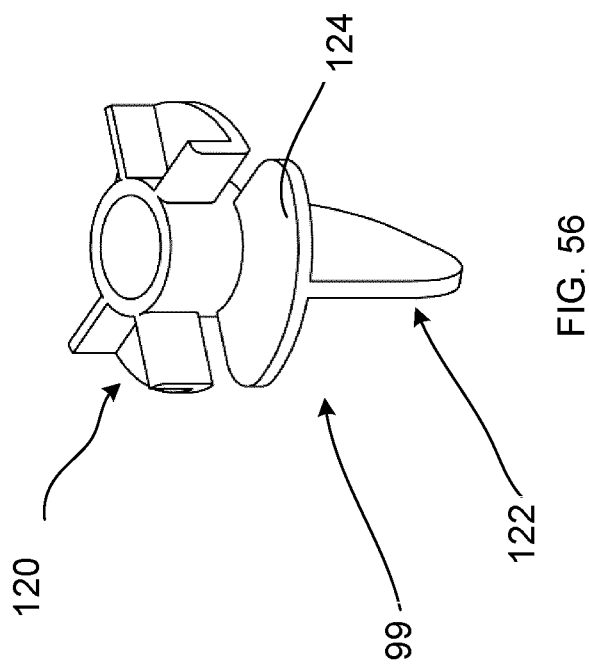
Figure 55:
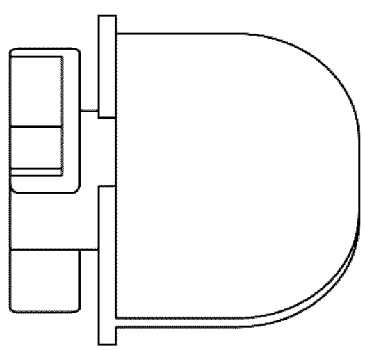
Figure 53:
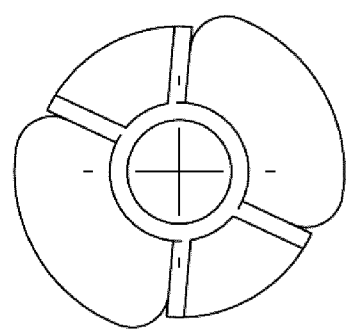
Figure 54:
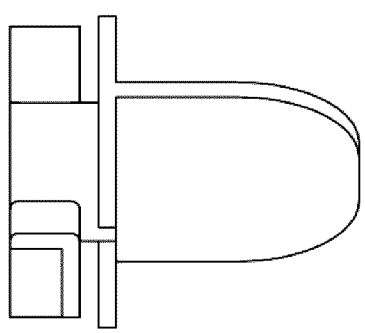

In some exemplary embodiments, for at least part of the dispensing mode, the fluid capsule carrier 40 is further configured to rotate axially between a lock-unaligned angular position (as generally shown in FIGS. 26 and 27) and a lock-aligned angular position (as generally shown in FIGS. 28 and 29). This may be provided, with reference to FIGS. 5 to 10, by at least one rotation interface, as will be described, which is provided across a pair of first cooperating elements respectively on the fluid capsule carrier 40 and at least one of the plunger structure 34 and the needle carrier 22. In the example shown in FIG. 5, the at least one rotation interface includes a first rotation interface 50 provided between the fluid capsule carrier 40 and the plunger structure 34, each including one of a corresponding first set of first cooperating elements, including at least one first guide path 54 and at least one first follower 56 to travel along the guide path 54. As can be seen in FIG. 5, the first guide path 54 is ramped, but may be other configurations such as stepped, or shaped in various ways, such as the angular shape shown, or alternatively shaped as a parabola or the like. Thus, in some exemplary embodiments, the complementary guide formations between the fluid capsule carrier 40 and the plunger 36 enable them to rotate together while the needle carrier 22 and the plunger support travel along the barrel toward the first dispensing position as shown in FIG. 28.

The first follower 56 in the first set of first cooperating elements is provided, in this example, as a follower flange 56 which extends laterally outwardly from a plunger support 38, forming an end region 56a. Thus, as the end region 56a travels along the first guide path 54 as shown by path B1, the plunger structure 34 rotates in a spiral about longitudinal axis A in a downward direction as viewed in FIG. 5.

Continuing with reference to FIG. 5, the fluid capsule carrier 40 includes a generally cylindrical capsule carrier body 40a with an open end region 40b, which is opposite the second fluid delivery end region 24 and receives the plunger structure 34 therethrough. A pair of symmetrically oriented projections 42 are positioned adjacent the open end region 40b with at least one, in this case two, first guide paths 54 formed on outward edge regions thereon. Thus, the first guide paths 54 are operatively oriented near the open end region to engage the corresponding pair of symmetrically disposed first followers 56 on the plunger structure 34.

Referring to FIGS. 2, 5, and 17 to 19a, in some exemplary embodiments, the at least one rotation interface includes a second rotation interface 60 provided between the fluid capsule carrier 40 and the needle carrier 22. Each includes one of a corresponding second set of second cooperating elements. In the case of the fluid capsule carrier 40, a pair of symmetrically oriented second guide paths 62 is located relative to the second fluid delivery end 24, and are formed by openings 62a in the cylindrical carrier body 40a. The second guide paths 62 are operatively oriented near the second fluid delivery end region 24 to align with, and engage, at least one second follower 61 on the needle carrier 22 (FIG. 17) which, in this case, is provided by way of a pair of second followers 64 as edge surfaces on an inner face 22b on the needle carrier 22. Thus, the capsule carrier body 40a provides a pair of first guide paths 54 and a pair of second guide paths 62, each pair being symmetrically arranged relative to the longitudinal axis A and interfacing with corresponding first followers 56 (on the plunger structure 34) and second followers 64 (on the needle carrier 22).

It will be understood that "guide path" and "follower" are relative terms to identify two components of an interface. Such terms are not intended to restrict the components to a particular function unique to a guide and a follower respectively, since they are both responding relative to one another to forces exerted externally. Thus, it may be considered that the guide paths are, in some examples, following the net forces exerted on the fluid capsule carrier 40 as forces between the plunger structure 34 and the needle carrier 22, or the barrel 12.

Thus, in some embodiments, each of the first and second rotation interfaces 50, 60 may provide two pairs of cooperating elements to guide rotation of the fluid capsule carrier 40 relative to the plunger structure and/or the needle carrier, in order to transfer the fluid capsule carrier to the lock-aligned angular position. As will be described, however, this relative rotation may also controllably enable the plunger to be released to pressurize the fluid capsule. Movement provided by both rotational interfaces may be controlled by a latch interface so that both actions occur in a designated manner.

Referring to FIGS. 2 to 4, the fluid capsule carrier 40 includes a fluid capsule receiving surface 44, which in this exemplary embodiment is generally transverse relative to the longitudinal axis A, and a needle passage 44a extending therethrough to receive the upstream end 26a of the needle 26 in the first dispensing position. Referring further to FIGS. 11 to 13, the plunger structure 34 includes a plunger end region 34a to travel during the dispensing mode toward a second dispensed position adjacent the capsule receiving surface 44 and to cooperate therewith to pressurize the fluid capsule 30, thereby to express the fluid through the needle 26.

Referring to FIGS. 3, 4, and 11 to 14, the plunger structure 34 includes a plunger 36 and a plunger support 38. As will be described, the plunger 36 is configured to swivel through at least a predetermined range about the longitudinal axis A and relative to the plunger support 38 so as to rotate together with the fluid capsule carrier 40. The plunger support includes a central circular passage 38d (FIG. 12a) which has an end region with a pair of opposed guide windows 38e. The plunger has a number of stabilizers 36b spaced therealong to engage the circular passage 38d, as well as a pair of opposed tabs 36a, each of which is received in a corresponding guide window 38e. Further, the fluid capsule carrier 40 and plunger 36 are configured to fix an angular position of the plunger 36 relative to the fluid capsule carrier 40 at least during the dispensing mode.

Referring to FIGS. 11 and 14, the fluid capsule carrier 40 and plunger 36 are provided with complementary guide formations, which includes at least one laterally (in this case the two) outwardly extending tabs 36a and a corresponding pair of longitudinal grooves 43 formed in an inner surface 40c of the fluid capsule carrier 40. Thus, the engagement of the tabs 36a with the grooves 43 configures the plunger support 38 to follow fluid capsule carrier 40, in the dispensing mode. The guide windows 38e thus allow for rotation of the tabs 36a within a designated angular range according to the width of the guide windows 38e.

In some exemplary embodiments, and as shown in FIGS. 17 and 24, the needle carrier 22 and barrel 12 may further include complementary formations aligned with the longitudinal axis A to form a needle carrier travel path along the longitudinal axis A, while inhibiting relative rotation of the needle carrier 22 relative to the barrel 12. In this case, the needle carrier 22 includes a pair of spaced flanges 22a which are aligned with the longitudinal axis A to engage corresponding spaced flanges 15 (FIG. 24) extending inwardly along the inner surface 12a of the barrel 12. In this case, the spacing between the flanges 22a is relatively larger than the spacing between the flanges 15, to receive the flanges 15 between the flanges 22a, though this configuration may be reversed or configured in other ways to inhibit relative rotation between the needle carrier and barrel. That said, there may in other exemplary embodiments in which relative rotation between the needle carrier and barrel may be beneficial.

Referring to FIG. 18, the needle carrier 22 is further provided with two pairs of central body structures which extend in a manner to define a lateral periphery and terminate at a corresponding pair of passages 25a which are each configured to receive one of a pair of locking tabs 72 (FIG. 20) on the fluid capsule carrier 40 during assembly. The lower boundary of the passage 25a, as viewed in FIG. 18, is tapered in a manner to permit one way travel of the locking tab downwardly. Installing of the fluid capsule carrier 40 with the needle carrier 22 thus involves passing the locking tabs 72 along each of the passages 25a and passed the tapered lower boundary, thus requiring a slight lateral flexing of the needle carrier according to arrows F to open the tapered lower boundary to allow the locking tabs therethrough.

Referring to FIGS. 2 to 4, 20 to 29, in some exemplary embodiments, the dispenser 10 may further comprise a lock interface 70 to fix the dispenser with needle carrier 22 in a retracted position at a locking location, when the fluid capsule carrier 40 is in a lock-aligned angular position. In this configuration, the downstream end 26b is retracted within the barrel 12, i.e. so that it is not projecting beyond the first fluid delivery end region 14. This may thus be achieved while the needle carrier 22 is biased to travel from the dispensed position to the locking location. In this case, the bias may be provided by at least one compression spring, in this case a pair of compression springs 80, acting between the first and second delivery end regions 14 and 24, and located in seating recesses 80a, 80b on the inwardly facing wall of the barrel 12 (FIG. 21a) and on the adjacent facing surface of the needle carrier 22 (FIG. 19a), respectively.

In some exemplary embodiments, both the latch and lock interfaces 46, 70 may utilize at least one, in this case the pair of opposed locking tabs 72 extending laterally outwardly from the fluid capsule carrier 40. In the case of the latch interface 46, the locking tabs 72 are each aligned with one of a pair of opposed symmetrical axial latch formations 74, one of which is shown in FIGS. 20 and 23, which extends along an inner surface 12a of the barrel 12 and terminating at a transition region 76. Each locking tab 72 is configured to travel (as shown by path D1) along a first adjacent region 74a of the axial latch formation 74 (in a lock-nonaligned angular position), during which time the axial latch formation 74 functions as a barrier to interrupt rotation of the fluid capsule carrier 40 about axis A, which would otherwise require lateral travel of the locking tabs 22 in the direction of their respective axial latch formations 74. Meanwhile, the latch interface 46 enables the body 20 to travel relative to the barrel 12 against the biasing action of the compression springs 80 which in the example of dispenser 10 may be overcome by the user pressing on the plunger structure 34 with the barrel 12 placed against the fluid delivery site. This travel is caused by compression force C acting between the plunger structure 34 and the barrel 12, against the opposing biasing force of compression springs 80.

Each axial latch formation 74 is bevelled in the transition region 76, as can best be seen in FIGS. 23 and 24, in a manner which takes into account (and in this example matches) the outer profile of the locking tab 72 (as can be seen in FIG. 26), enabling the latter to pass over the transition region 76, to a lock-aligned angular position (shown in FIG. 28) during rotational movement of the fluid capsule carrier 40 relative to the needle carrier 22. Thus, the latch interface 70 is released, once the locking tabs 72 pass through their respective transition regions 76, as occurs along path D2.

When in the lock-aligned angular position, the fluid capsule carrier 40 is thus movable axially under the action of the plunger structure 34, against the biasing force of the compression springs 80, corresponding to the locking tabs 72 travelling along path D3. This position may correspond to, or be upstream of, the piercing of the membrane 30a by the upstream end 26a of the needle 26. In either case, the fluid capsule 30 may move axially in the direction of the needle 26 until the plunger end region 34a engages the fluid capsule 30, thereby cooperating with the transverse capsule receiving surface 44 to pressurize the fluid capsule 30 and forcing fluid through the needle to exit from the downstream end 26b. The plunger end region 34a reaches a dispensed position when it fully engages the transverse capsule receiving surface 44, via a collapsed (and essentially empty or void) fluid capsule. Meanwhile, the locking tabs 72 are in their lock-aligned positions, but not yet at their locking location.

In some exemplary embodiments, as can be seen in FIG. 23, the lock interface may be provided between the locking tabs 72, when in their lock-aligned angular positions, and a transverse locking flange 78 extending transversely across the surface of the barrel 12 and positioned at a location adjacent to the transition region 76, and corresponding to a designated locking location, and which is located on a second region 74b of the locking edge formation. The locking tabs 72 may thus be configured, with release of the fluid capsule carrier 40 and under the consequent bias of compression springs 80, to travel along path E toward and pass over the transverse locking flange 78, under the action of their live hinge resiliency, to a locking location, as shown in FIG. 29. In this position, the locking tabs are behind and against their respective locking flanges 78, thus prevented from travelling back toward the first fluid delivery end region 14.

Thus, in some exemplary embodiments, the latch interface 46 and the lock interface 70 may provide for both controlled dispensing of fluid and for a locking of the dispenser with the needle 26 in a retracted position within the barrel 12 following dispensing.

Referring to FIGS. 4, 17 and 32 to 35, in some exemplary embodiments, the dispenser 10 may be provided with a lock interface 70 between locking tabs 38f on the plunger support 38 (as can be seen in FIG. 4) and aligned bosses 22c on the needle support 22 (FIG. 17), to lock the plunger support 38 (and hence the plunger 36) and the needle support 22 following fully dispensing of the contents of the fluid capsule 30. Interaction between the locking tabs 38f and bosses 22c may be seen in successive unlocked and locked positions shown by FIGS. 34 and 35.

In the fully dispensed position, as shown in FIG. 35, the upstream end 26a of the needle 26 is shown extending into the needle passage 44a, and thus piercing both sides of the fluid capsule 30 at this stage. That said, the capsule, the needle and/or the needle passage 44a may be mutually configured to allow the fluid capsule to gather into the needle passage 44a or otherwise not to be penetrated by the needle.

Thus, as the plunger support 38 approaches the fully dispensed position, the locking tabs 38f flex over the corresponding locking formations, in this exemplary embodiment in the form of bosses 22c. Due to their live hinge resiliency, the locking tabs 38f may be configured to audibly "click" into the locked position as shown in FIG. 35 when reaching the fully dispensed position. Thus, the lock interface 70 achieves, in this instance, two roles. Firstly, it secures the plunger support 38 (and thus the plunger 36) with the needle carrier 22 in a locked configuration, so that further displacement to the locked position along path E, as shown in FIG. 23, may occur with the plunger support 38, the plunger 36 and the needle carrier 22 traveling in unison.

Secondly, the locking tabs 38f are one example of a configuration to emit an audible sound or other signal indicative of the use of the dispenser 10 reaching the second dispensed position. That said, the dispenser 10 may be configured in other ways to emit a sound audible to a user of the dispenser 10 indicative of the plunger 36 reaching the second dispensed position, as may be provided by other noise emitting configurations including other mechanical configurations using one or more biased noise emitting elements, either through the use of natural material resiliency, springs, magnetics or the like, or electronically through a noise emitting position sensor or the like.

Referring to FIG. 25, the dispenser 10 further comprises at least one, and in this instance a pair of user gripping tabs 84 extending outwardly from the needle carrier 22 for a user to engage with two fingers for manipulating the dispenser 10, through the dispensing mode.

Thus, in some exemplary embodiments, the actions of the dispenser 10 may involve, in sequence, a release mode in which the dispenser 10 transitions from a pre-dispensing locked configuration which enables the dispenser 10 to be manufactured, packaged and shipped to a dispensing site with reduced risk of incidental release of the fluid contained in fluid capsule 30, that is by inhibiting conditions during shipping or preparations that would deliver force C to the dispenser. The dispensing site may be, for instance, at a remote location and staffed by volunteer users who may not be practiced in the operation of a standard syringe. Further, the pre-dispensing locked configuration enables the dispenser 10 to be unpackaged and prepared for dispensing, with reduced risk of inadvertent contact with the needle, and with reduced risk of inadvertent dispensing of the fluid. At this time the dispenser 10, and the fluid delivery site on a patient, may be prepared.

To dispense the fluid, the user may grip the dispenser 10 by engaging the user gripping tabs 84 with the index and middle fingers and an outer end region of the plunger structure 34 with the thumb. In this condition, the dispenser 10 is locked from dispensing as a result of the engaged latch interface 46, that is by the locking tabs 72 of the corresponding axial latch formations 74 (FIG. 25), that is being located in the first adjacent region 74a (as shown in FIG. 23), thus preventing rotation of the fluid capsule carrier 40 relative to the needle carrier 22 and the plunger structure 34. Without that rotation, the plunger structure 34 is unable to travel toward the fluid capsule carrier 40 to pressurize the fluid capsule 30. However, in this configuration, the plunger structure 34 is moveable longitudinally relative to the barrel 12 when compressive force C is exerted on the compression springs 80, which occurs when the dispenser 10 is placed on and pressed against the fluid delivery site on the patient.

Referring to FIGS. 23 and 25, under compressive force C, the dispenser 10 moves toward the transition from the pre-dispensing locked mode (corresponding to path D1 of FIG. 23) to the dispensing mode, which occurs when the locking tabs 72 reach and traverse the bevelled transition regions 76 on the axial latch formations 74 (FIG. 25), along path D2. Thus the dispensing mode involves a first rotation phase during which the fluid capsule carrier 40 rotates relative to the needle carrier 22, as seen by the movement of the tabs 72 to their position shown in FIG. 28 (corresponding to path D2 of FIG. 23). The first and second followers 56 and 64 may then travel along the first and second guide paths 54, 62 (corresponding to path D3 of FIG. 23), with corresponding axial movement of the plunger end region 34a toward engagement with the fluid capsule 30. Thus, FIGS. 27 and 28 show a first rotation phase during which the fluid capsule carrier 40 rotates relative to the needle carrier 22 about the longitudinal axis A, while the plunger end region 34a approaches the capsule receiving surface 44. This can be seen by the corresponding follower member travelling along the guide surface from a starting position, which will depend on the relative configurations of the guide surface and the follower member, though in the illustrated example is a central location the guide surface.

Thus, (and referring to FIG. 5) during the first rotation phase, the first followers 56 travel along the first guide paths 54, in the direction of path B1, occurring together with travel of the tabs 72 along path D2. The first followers 56 then reach the onset of a second dispensing phase as they pass beyond the first guide paths and downwardly, as viewed in FIG. 2, in the direction of path B2, which corresponds to travel of the tabs 72 along path D3 (in FIG. 29). It will be understood that the separate paths D2 and D3 are exemplary and, in some cases, may be axial and tangential components of a helical path about longitudinal axis A.

In some exemplary embodiments, in the second dispensing phase, the point in travel of the first follower 56 at the transition point between arrows B1 and B2, may be configured to correspond generally to the beginning of contact between the plunger end region 34a and the capsule 30, while the travel of the first follower 56 generally ends at, or near, a limit surface 40d at the open end region 40b, as the plunger end region reaches engagement with the transverse capsule receiving surface 44 and thus a substantial completion of the dispensing of fluid in the fluid capsule 30 between them. It thus follows that the travel of the first follower 56 from the transition point toward the limit surface 40d corresponds to the dispensing of the fluid. Thus, the dispensing mode includes a second dispensing phase during which the plunger end region 34a is movable axially relative to the capsule receiving surface 44 toward the second dispensed position to pressurize the fluid capsule 30 and dispense the fluid.

The locking mode then follows by the release of the plunger 36 and the gripping tabs 84, thus causing the compression springs 80 to bias the body 20, and thus the locking tabs 72 towards their locked position with the locking flange 78 as shown in FIG. 29.

Referring to FIGS. 3, 20, 23, 25 and 26, another lock interface is shown at 88 (FIG. 25) and is provided by a complementary formation, in the form of a boss 12c in the side wall of the barrel 12, and located immediately above a passage shown at 12b. The boss 12c is aligned with a tab 22d (FIG. 26) outwardly extending from the needle carrier 22, which engages the boss 12c when the needle carrier is assembled with the barrel at the onset of the dispensing mode, as can be seen in FIG. 25. The lock interface 88 in this case is provided to lock the needle carrier 22 in position by engaging the tab 22d with the boss 12c. The passage 12b is provided in this case to enable them to be disassembled. In a commercial setting, the passage 12b may not be required and may thus be omitted, thus making the needle carrier effectively permanently installed in the barrel once the tab 22d and boss 12c are engaged.

Referring to FIGS. 3 to 10, looking more closely at the fluid capsule 30, even though the membrane 30a is shown to be relatively convex in FIGS. 3 and 4, which may occur in some cases when in a filled condition. On the other hand, the membrane 30a may also maintain a planar configuration. In either case, the membrane is joined to a spherical body 30b, by way of an ultrasonic weld seam or the like. The membrane 30a, by its flexible nature, will follow the shape of the transverse capsule receiving surface which is slightly concave to provide for a functional seating of the outer surface of the membrane 30a therein. When the fluid capsule 30 is in position on the fluid capsule carrier 40, the spherical body 30b is thus aligned with and engages the exposed surface 34b of the plunger end region 34a. The generally convex shape of the exposed surface 34b of the plunger (that is exposed to the fluid capsule 30) is complementary with the generally concave shape of the transverse fluid capsule receiving surface so that, when pressed together, they may substantially completely evacuate the cavity when reaching the dispensed position, as shown in FIG. 10. Thus, as the surface 34b approaches surface 44, internal pressure in the fluid capsule 30 increases to result in lateral tension on the membrane 30a which tends to stretch the membrane, in other words in a manner that will tend to increase the surface area of the membrane 30a. Thus, the tension in the membrane 30a enhances the piercing thereof by the upstream end 26a of the needle 26, to minimize a tendency that may otherwise arise for the membrane material to gather around the needle and thus delaying the onset of needle penetration and dispensing.

The transition between the membrane 30a and the spherical body 30b may be formed between a base layer and a cover layer, wherein the base layer has a planar zone to define the membrane 30a and a spherical region to define the spherical body 30b.

Referring to FIGS. 36 to 52, another fluid dispenser is shown at 92 comprising a barrel 94 terminating at a first fluid delivery end region 96 and a body 98. A cap 99 is provided to close a passage 96a (FIG. 49) in the delivery end region 96. In this case, the barrel 94 includes a pair of user gripping tabs 100 extending outwardly therefrom, enabling a user to establish a compressive force C between the barrel (via the user gripping tabs 100) and the body 98, without having to press the first fluid delivery end region 96 against a dispensing site, for example on a patient. In other words, the compressive force C may be established before any contact is made between the first fluid delivery end region 96 and the patient.

Referring to FIGS. 40 to 48, the body 98 includes a plunger support 102, plunger 103, and a needle carrier 104 (with passage 104a to carry the needle 105) which may be configured with formations, together with the barrel 94, to form a guide interface 108 for minimizing rotational movement therebetween. In this example, the guide interface 108 includes at least one support passage (in this case a pair of support passages 110) on the plunger support 102 which receive corresponding extended sections 106 on the barrel 96. In this case, the pair of support passages 110 are provided by a pair of symmetrically opposed circumferentially extended webs 114, each defining an outer periphery of one of a corresponding pair of support passages. Further, the plunger support 102 has a pair of ridged surface regions 118 between the webs 114 and which engage a corresponding pair of grooved guide portions 112.

In use, the plunger support 102 thus moves relative to the needle carrier 104 and the barrel 94, causing the guide portions 112 to travel along the ridged surface regions 118, while the extended sections 106 travel along the corresponding support passages 110, thus permitting longitudinal travel along axis A, with relative rotational movement of the plunger support 102, the needle carrier 104 and the barrel 94 blocked by the confining of the extended sections 106 to the boundaries of the support passages 110. Other configurations may be deployed to minimize rotational movement. Further, there may be some configurations in which rotational movement between the plunger support 102 and the needle carrier 104 may provide a useful functional purpose in some cases.

Referring to FIGS. 49 and 53 to 56, the cap 99 is provided with a bow tie shaped coupler 120 having an activating flange 122 to be held by the user, which fits the similar bow tie shape of the passage 96a, along with a base flange 124. Thus, installation of the cap 99 involves aligning up the coupler 120 with the passage 96a and extending the coupler 120 into the passage 96a until the base flange 124 engages the outer surface of the first fluid dispensing end 96. The cap 99 may then be rotated to bring the coupler 120 out of alignment with the passage, with the structure of the first fluid dispensing end 96 held between the coupler 120 and the base flange 124, thus holding the cap 99 in place, until it is to be used. If desired, one or more further configurations may be provided to return the cap 99 in place, by providing additional frictional or latch configurations between the cap 99 and the structure of the first fluid dispensing end 96.

Thus, in some exemplary embodiments as the dispenser 92, the plunger 103 and the fluid capsule carrier 128 provide a capsule receiver, which is configured to form a fluid capsule pressuring zone 126 in a first capsule pressurizing mode. The needle carrier 104 supports a fluid delivery needle, and wherein the needle carrier and the fluid capsule receiver are configured to cause the needle to extend into the capsule pressurizing zone to pierce the pressurized fluid capsule in a second fluid capsule piercing mode. The fluid capsule carrier 128 and the needle carrier 104 are configured to move along the body 98 to expose a fluid delivery end of the needle 105 for a third fluid delivery mode.

In this case, the plunger 103 and fluid capsule carrier 128 have complementary surfaces to locate the fluid capsule therebetween. At least one interface is thus operable between the plunger support 102, the fluid capsule carrier 128, the needle carrier 104 and/or the body 98 to enable displacement of the plunger relative to the fluid capsule carrier in the first, second and third modes while exerting a compressive force at substantially consistent magnitude between the plunger support and the body Thus, in some exemplary embodiments, the dispenser may configured to provide a method or approach to secure the dispensing device following delivery of a fluid therefrom, by providing a barrel defining a longitudinal axis terminating at a first fluid delivery end region and a dispenser body movable along the barrel relative to the first fluid delivery end region. The dispenser body may then be displaced in a first phase between a pre-dispensing configuration and a dispensed configuration, and in a second phase between the dispensed configuration and a locked post-dispensing configuration, wherein the dispenser body may be rotated about the longitudinal axis, at least in part, during the first phase and/or the second phase for aligned orientation with at least one locking structure so that the dispenser may be locked during travel in the second phase. Thus, structure features of exemplary embodiments herein may be utilized without necessarily requiring the action to align the dispenser body with the at least one locking structure to occur in the first phase. Rather, the second phase may be configured in some cases to provide the alignment, or a combination of the first and second phases.

Thus, some exemplary embodiments, for example the dispenser 92, enable a method of dispensing a fluid from a fluid capsule, comprising:
 a. locating a fluid capsule on a fluid capsule support surface defined in a fluid capsule;
 b. displacing a plunger along an axis to toward engagement with the fluid capsule;
 c. pressurizing the fluid capsule between the plunger and the fluid capsule support so that a membrane of the fluid capsule against the fluid capsule support surface is in a tensioned needle receiving configuration;
 d. displacing the plunger and the fluid capsule support, with the fluid capsule in the needle receiving configuration toward a needle support to cause a fluid capsule-piercing end of a fluid delivery needle to extend through the fluid capsule support surface to penetrate the membrane to initiate onset of dispensing of fluid through the needle; and
 e. advancing the plunger, the fluid capsule support and the needle support toward a fluid delivery configuration with an opposite fluid delivery end of the needle exposed to penetrate a user's skin.

Clauses:

Exemplary embodiments as described herein, including dispensers and methods, are described in the following clauses:
 1. A fluid dispenser comprising a barrel defining a longitudinal axis terminating at a first fluid delivery end region; a dispenser body movable along the barrel relative to the first fluid delivery end region in a first phase between a pre-dispensing configuration and a dispensed configuration, and in a second phase between the dispensed configuration and a locked post-dispensing configuration, wherein the dispenser body is configured to rotate about the longitudinal axis during the first phase for aligned orientation with at least one locking structure configured to lock the dispenser body in the locked post-dispensing configuration during travel in the second phase.

2. A dispenser as defined in any of the preceding or following clauses, wherein the dispenser body includes a needle carrier with a second fluid delivery end region defined thereon.

3. A dispenser as defined in any of the preceding or following clauses, wherein the needle carrier is configured to be in a retracted position within the barrel in the locked post-dispensing configuration.

4. A dispenser as defined in any of the preceding or following clauses, wherein the dispenser body includes a fluid capsule carrier moveable relative to the needle carrier in the first phase to dispense fluid from a carried capsule.

5. A dispenser as defined in any of the preceding or following clauses, wherein the dispenser body includes a plunger structure movable relative to the fluid capsule carrier in at least part of the first phase to pressurize a carried capsule.

6. A dispenser as defined in any of the preceding or following clauses, wherein the fluid capsule carrier is configured, during at least part of the first phase, to travel with the plunger structure.

7. A dispenser as defined in any of the preceding or following clauses wherein, during at least part of the first phase, the fluid capsule carrier is configured to rotate axially between lock-unaligned and lock-aligned angular positions.

8. A dispenser as defined in any of the preceding or following clauses, further comprising at least one rotation interface defined across a plurality of cooperating elements respectively on the fluid capsule carrier and at least one of the plunger structure and the needle carrier, to enable axial rotation of the fluid capsule carrier relative to the barrel.

9. A dispenser as defined in any of the preceding or following clauses, wherein the at least one rotation interface includes a first rotation interface provided between the fluid capsule carrier and the plunger structure, each including one of a corresponding first set of first cooperating elements.

10. A dispenser as defined in any of the preceding or following clauses, wherein the at least one rotation interface includes a second rotation interface provided between the fluid capsule carrier and the needle carrier, each including one of a corresponding second set of second cooperating elements.

11. A dispenser as defined in any of the preceding or following clauses, wherein the first and/or second cooperating elements include at least one guide path and at least one follower to travel along the guide path.

12. A dispenser as defined in any of the preceding or following clauses, wherein the guide path is ramped.

13. A dispenser as defined in any of the preceding or following clauses, wherein the fluid capsule carrier includes a capsule carrier body comprising an open end region opposite the second fluid delivery end region to receive the plunger structure therethrough.

14. A dispenser as defined in any of the preceding or following clauses, wherein the at least one first guide path is operatively oriented near the open end region to engage the first follower on the plunger structure.

15. A dispenser as defined in any of the preceding or following clauses, wherein the second guide path is operatively oriented near the second fluid delivery end region to engage the second follower on the needle carrier.

16. A dispenser as defined in any of the preceding or following clauses, wherein the capsule carrier body is cylindrical and includes a pair of first guide paths and a pair of second guide paths, each pair being symmetrically arranged relative to the longitudinal axis.

17. A dispenser as defined in any of the preceding or following clauses, wherein the fluid capsule carrier includes a transverse fluid capsule receiving surface, and a needle passage extending therethrough to receive an upstream end of a needle.

18. A dispenser as defined in any of the preceding or following clauses, wherein the plunger structure includes a plunger end region to travel during at least part of the first phase toward the fluid capsule receiving surface to pressurize the fluid capsule, thereby to express the fluid through the needle.

19. A dispenser as defined in any of the preceding or following clauses, wherein the first phase includes at least in part:
   a. a first rotation phase during which the fluid capsule carrier is rotatable relative to the needle carrier about the longitudinal axis, as the plunger end region approaches the fluid capsule receiving surface; and
   b. a second dispensing phase during which the plunger end region is movable axially relative to the fluid capsule receiving surface, at least in part, to pressurize the fluid capsule.

20. A dispenser as defined in any of the preceding or following clauses, wherein during the second dispensing phase, at least in part, the plunger end region is movable axially with the fluid capsule receiving surface, toward piercing contact with a needle on the needle carrier, to dispense the fluid.

21. A dispenser as defined in any of the preceding or following clauses, wherein the at least one locking structure includes a lock interface to fix the dispenser body at a locking location when the dispenser body is in the lock-aligned angular position.

22. A dispenser as defined in any of the preceding or following clauses, wherein the needle carrier is biased to travel from the second dispensed position to the locking location.

23. A dispenser as defined in any of the preceding or following clauses, wherein the lock interface is configured between the fluid capsule carrier and the barrel to engage when the dispenser is in the lock-aligned angular position.

24. A dispenser as defined in any of the preceding or following clauses, further comprising at least one latch structure extending laterally outwardly from the fluid capsule carrier and at least one axial latch edge formation extending along an inner surface of the barrel and terminating at a transition region, wherein the latch structure is configured to travel along the axial latch edge formation toward and beyond the transition, thereby to release the plunger structure.

25. A dispenser as defined in any of the preceding or following clauses, wherein the at least one locking structure and the at least one latch structure are each defined in common by a pair of locking tabs extending outwardly from the fluid capsule carrier.

26. A dispenser as defined in any of the preceding or following clauses, wherein the bias is provided by at least one spring acting between the first and second fluid delivery end regions.
27. A dispenser as defined in any of the preceding or following clauses, wherein the lock interface is configured between the at least one locking structure extending laterally outwardly from the needle carrier and at least one transverse locking edge formation extending transversely across a surface of the barrel at the locking location, wherein the locking structure is configured to travel toward and engage the transverse locking edge formation at the locking location when in the lock-aligned angular position.
28. A dispenser as defined in any of the preceding or following clauses, wherein the at least one locking structure includes at least one locking tab extending laterally outwardly from the fluid capsule carrier to engage a corresponding locking edge formation on the barrel.
29. A dispenser as defined in any of the preceding or following clauses, wherein the plunger structure includes a plunger and a plunger support, the plunger configured to swivel through at least a predetermined range relative to the plunger support to rotate with the fluid capsule carrier.
30. A dispenser as defined in any of the preceding or following clauses, the fluid capsule carrier and the plunger being configured to fix an angular position of the plunger relative to the fluid capsule carrier at least during the first phase.
31. A dispenser as defined in any of the preceding or following clauses, the fluid capsule carrier and the plunger further comprising complementary guide formations to align the plunger with the fluid capsule carrier.
32. A dispenser as defined in any of the preceding or following clauses, wherein the guide formations include at least one laterally outwardly extending tab on the plunger and at least one longitudinal groove formed in an inner surface of the fluid capsule carrier.
33. A dispenser as defined in any of the preceding or following clauses, wherein the plunger support and the needle carrier are configured to fix an angular position of the plunger support relative to the needle carrier.
34. A dispenser as defined in any of the preceding or following clauses, wherein the needle carrier and the plunger support include complementary formations aligned with the longitudinal axis to form a plunger support travel path along the longitudinal axis.
35. A dispenser as defined in any of the preceding or following clauses, wherein the complementary formations include a pair of flanges extending from one of the needle carrier and the plunger support, to be received in complementary groove formations on the other of the needle carrier and the plunger support.
36. A dispenser as defined in any of the preceding or following clauses, wherein the plunger support includes a cover flange laterally outwardly spaced to form an annular passage to receive an adjacent end region on the barrel.
37. A dispenser as defined in any of the preceding or following clauses, further comprising at least one user gripping tab extending outwardly from the needle carrier or the barrel for a user to engage for manipulating the dispenser through at least part of the first phase.
38. A dispenser as defined in any of the preceding or following clauses, further comprising a signal emitter to emit a signal indicating that the plunger structure has reached a dispensed position.
39. A dispenser as defined in any of the preceding or following clauses, wherein the signal emitter includes a signal emitting interface between the barrel and the dispenser body.
40. A dispenser as defined in any of the preceding or following clauses, wherein the signal emitting interface includes at least one resilient tab and at least one locking formation aligned therewith, each of which is located on one a respective one of the barrel and the dispenser body.
41. A dispenser as defined in any of the preceding or following clauses, wherein the at least resilient tab extends from the plunger support and the at least one locking formation is positioned on an inner surface of the barrel.
42. A dispenser as defined in any of the preceding or following clauses, wherein the at least one resilient tab is locked in position with at least one locking formation in the dispensed position.
43. A dispenser as defined in any of the preceding or following clauses, further comprising a lock interface to lock the dispenser body relative to the barrel in the dispensed position.
44. A dispenser as defined in any of the preceding or following clauses, wherein the lock interface includes at least one resilient tab and a boss aligned therewith, each of which is located on one a respective one of the barrel and the body.
45. A dispenser as defined in any of the preceding or following clauses, wherein the resilient tab extends from the plunger support and the boss is positioned on an inner surface of the barrel.
46. A dispenser as defined in any of the preceding or following clauses, wherein the plunger support, the needle carrier and/or the barrel include formations to form a guide interface for inhibiting rotational movement therebetween.
47. A dispenser as defined in any of the preceding or following clauses, wherein the guide interface includes at least one support passage to receive an extended section on the barrel.
48. A dispenser as defined in any of the preceding or following clauses, wherein the plunger support includes a pair of symmetrically opposed circumferentially extended webs, each defining an outer periphery of one of a corresponding pair of support passages.
49. A dispenser as defined in any of the preceding or following clauses, wherein the needle carrier includes a pair of opposed and circumferentially cross sectioned guide sections to engage corresponding surfaces on the plunger support.
50. A fluid dispenser comprising:
   a. a barrel defining a longitudinal axis terminating at a first fluid delivery end region;
   b. a body movable along the barrel relative to the first fluid dispensing end region, the body including:
      i. a needle carrier aligned with the longitudinal axis and terminating at a second fluid delivery end region, at which is located a needle having a downstream end configured to project through the first fluid delivery end region in a first dispensing position;

ii. a plunger structure aligned with the longitudinal axis and movable axially relative to the needle carrier; and
iii. a fluid capsule carrier which is configured to receive a fluid capsule, the fluid capsule carrier being aligned with the longitudinal axis and movable axially relative to the needle carrier and the plunger structure;
iv. a latch interface operable under the action of a compressive force between the barrel and the body, to release the plunger structure to travel relative to the needle carrier; and
v. the fluid capsule carrier configured, in a dispensing mode, to travel toward piercing contact of the needle with the fluid capsule.

51. A dispenser as defined in clause any of the preceding or following clauses, wherein the fluid capsule carrier is configured, in at least part of the dispensing mode, to travel with the plunger structure.

52. A dispenser as defined in any of the preceding or following clauses, wherein, in at least part of the dispensing mode, the fluid capsule carrier is configured to rotate axially between lock-unaligned and lock-aligned angular positions.

53. A dispenser as defined in any of the preceding or following clauses, further comprising at least one rotation interface including a plurality of cooperating elements respectively on the fluid capsule carrier and at least one of the plunger structure and the needle carrier.

54. A dispenser as defined in any of the preceding or following clauses, wherein the at least one rotation interface includes a first rotation interface provided between the fluid capsule carrier and the plunger structure, each including one of a corresponding first set of first cooperating elements.

55. A dispenser as defined in any of the preceding or following clauses, wherein the at least one rotation interface includes a second rotation interface provided between the fluid capsule carrier and the needle carrier, each including one of a corresponding second set of second cooperating elements.

56. A dispenser as defined any of the preceding or following clauses, wherein the first and/or second cooperating elements include at least one guide path and at least one follower to travel along the guide path.

57. A dispenser as defined in any of the preceding clauses, wherein the guide path is ramped.

58. A dispenser as defined in any of the preceding or following clauses, wherein the follower in the first and/or second sets of cooperating elements includes a follower guide path.

59. A dispenser as defined in any of the preceding or following clauses, wherein the fluid capsule carrier includes a capsule carrier body comprising an open end region opposite the second fluid delivery end region to receive the plunger structure therethrough, 60. A dispenser as defined in any of the preceding or following clauses, wherein at least one first guide path is operatively oriented near the open end region to engage the first follower on the plunger structure, and at least one second guide path operatively oriented near the second fluid delivery end region to engage the second follower on the needle carrier.

61. A dispenser as defined in any of the preceding or following clauses, wherein the capsule carrier body is cylindrical and includes a pair of first guide paths and a pair of second guide paths, each pair being symmetrically arranged relative to the longitudinal axis.

62. A dispenser as defined in any of the preceding or following clauses, wherein the fluid capsule carrier includes a fluid capsule receiving surface, and a needle passage extending therethrough to receive the upstream end of the needle in the first dispensing position, the plunger structure including a plunger end region to travel during the dispensing mode toward a second dispensed position adjacent the fluid capsule receiving surface and to cooperate therewith to pressurize the fluid capsule, thereby to express the fluid through the needle.

63. A dispenser as defined in any of the preceding or following clauses, wherein the dispensing mode includes at least in part:
a. a first rotation phase during which the fluid capsule carrier rotates relative to the needle carrier about the longitudinal axis, while the plunger end region approaches the fluid capsule receiving surface; and
b. a second dispensing phase during which the plunger end region is movable axially relative to the fluid capsule receiving surface, at least in part, to pressurize the fluid capsule and dispense the fluid.

64. A dispenser as defined in any of the preceding or following clauses, wherein during the second dispensing phase, at least in part, the plunger end region is movable axially with the fluid capsule receiving surface, toward piercing contact with a needle on the needle carrier, to dispense the fluid.

65. A dispenser as defined in any of the preceding or following clauses, further comprising a lock interface to fix the body at a locking location when the fluid capsule carrier is in the lock-aligned angular position.

66. A dispenser as defined in any of the preceding or following clauses, wherein the needle carrier is biased to travel from the second dispensed position to the locking location.

67. A dispenser as defined in any of the preceding or following clauses, wherein the bias is provided by at least one spring acting between the first and second fluid delivery end regions.

68. A dispenser as defined in any of the preceding or following clauses, further comprising a latch interface configured between at least one locking tab extending laterally outwardly from the fluid capsule carrier and at least one axial latch edge formation extending along an inner surface of the barrel and terminating at a transition region, wherein the locking tab is configured to travel along the axial locking edge formation under the action of the compressive force toward and beyond the transition region, thereby to release the plunger structure for travel relative to the fluid capsule carrier.

69. A dispenser as defined in any of the preceding or following clauses, wherein the lock interface is configured between at least one locking tab extending laterally outwardly from the fluid capsule carrier and at least one transverse locking edge formation extending transversely across an inner surface of the barrel at the lock location, wherein the locking tab is configured to travel toward and engage the transverse locking edge formation at the locking location when in the lock-aligned angular position.

70. A dispenser as defined in any of the preceding or following clauses, wherein the at least one locking tab includes a pair of locking tabs extending laterally outwardly from the fluid capsule carrier.

71. A dispenser as defined in any of the preceding or following clauses, wherein the plunger structure includes a plunger and a plunger support, the plunger configured to swivel through at least a predetermined range relative to the plunger support to rotate with the fluid capsule carrier.

72. A dispenser as defined in any of the preceding or following clauses, the fluid capsule carrier and the plunger being configured to fix an angular position of the plunger relative to the fluid capsule carrier at least during the dispensing mode.

73. A dispenser as defined any of the preceding or following clauses, the fluid capsule carrier and the plunger further comprising complementary guide formations.

74. A dispenser as defined in any of the preceding or following clauses, wherein the guide formations include at least one laterally outwardly extending tab on the plunger and at least one longitudinal groove formed in an inner surface of the fluid capsule carrier.

75. A dispenser as defined in any of the preceding or following clauses, wherein the plunger support and the needle carrier are configured to fix an angular position of the plunger support relative to the needle carrier in the dispensing mode.

76. A dispenser as defined in any of the preceding or following clauses, wherein the needle carrier and the plunger support include complementary formations aligned with the longitudinal axis to form a plunger support travel path along the longitudinal axis.

77. A dispenser as defined in any of the preceding or following clauses, the complementary formations including a pair of flanges extending from the needle carrier toward the plunger support, to be received in complementary groove formations on the plunger support.

78. A dispenser as defined in any of the preceding or following clauses, wherein the plunger support includes a cover flange laterally outwardly spaced to form an annular passage to receive an adjacent end region on the barrel.

79. A dispenser as defined in any of the preceding or following clauses any, further comprising at least one user gripping tab extending outwardly from the needle carrier or the barrel for a user to engage for manipulating the dispenser through at least part of the dispensing mode.

80. A dispenser as defined in any of the preceding or following clauses, further comprising a signal emitter to emit a signal indicating that the plunger structure has reached the second dispensed position.

81. A dispenser as defined in any of the preceding or following clauses, wherein the signal emitter includes a signal emitting interface between the barrel and the body.

82. A dispenser as defined in any of the preceding or following clauses, wherein the signal emitting interface includes at least one resilient tab and at least one locking formation aligned therewith, each of which is located on one a respective one of the barrel and the body.

83. A dispenser as defined in any of the preceding or following clauses, wherein the resilient tab extends from the plunger support and at least one locking formation is positioned on an inner surface of the barrel.

84. A dispenser as defined any of the preceding or following clauses, wherein the resilient tab is locked in position with the at least one locking formation in the second dispensed position.

85. A dispenser as defined in any of the preceding or following clauses, further comprising a lock interface to lock the body relative to the barrel in the second dispensed position.

86. A dispenser as defined in any of the preceding or following clauses, wherein the lock interface includes at least one resilient tab and a boss aligned therewith, each of which is located on a respective one of the barrel and the body.

87. A dispenser as defined in any of the preceding or following clauses, wherein the resilient tab extends from the plunger support and the boss is positioned on an inner surface of the barrel.

88. A dispenser as defined in any of the preceding or following clauses, wherein the plunger support, the needle carrier and/or the barrel include formations to form a guide interface for guiding movement therebetween.

89. A dispenser as defined in any of the preceding or following clauses, wherein the guide interface includes at least one support passage to receive an extended section on the barrel.

90. A dispenser as defined in any of the preceding or following clauses, wherein the plunger support includes a pair of symmetrically opposed circumferentially extended webs, each defining an outer periphery of one of a corresponding pair of support passages.

91. A dispenser as defined in any of the preceding or following clauses, wherein the needle carrier includes a pair of opposed and circumferentially cross sectioned guide sections to engage corresponding surfaces on the plunger support.

92. A fluid dispenser comprising a barrel defining a longitudinal axis and terminating at a first fluid delivery end region; a body movable along the barrel relative to the first fluid delivery end region, the body including a needle carrier, a plunger and a fluid capsule carrier therebetween, a latch interface between the body and the barrel and responsive to a release force therebetween caused by compressive engagement of the barrel at a fluid delivery site, to enable travel of the plunger and the fluid capsule carrier toward the needle carrier, to a dispensing configuration in which an upstream end of a needle on the needle carrier extends into a capsule carrying region of the fluid capsule carrier and a downstream end of the needle projects extends through the first fluid delivery end region for delivery of a fluid thereto.

93. A fluid dispenser comprising a barrel defining a longitudinal axis terminating at a dispensing end; a dispenser body movable along the barrel relative to the dispensing end, the dispenser body including a needle carrier, a plunger and a fluid capsule carrier moveable relative to the needle carrier and the plunger, and a latch interface configured to release the dispenser body for travel in the barrel in response to a release force between the barrel and the dispenser body.

94. A fluid dispenser comprising a barrel defining a longitudinal axis terminating at a dispensing end; a dispenser body movable along the barrel relative to the dispensing end, the dispenser body including a needle carrier, a plunger and a fluid capsule carrier moveable relative to the needle carrier and the plunger, and a latch interface configured to release the dispenser body for dispensing travel in the barrel in response to a compressive engagement of the dispensing end at a fluid delivery site.

95. A fluid dispenser, comprising a fluid capsule receiver configured to form a fluid capsule pressuring zone in a first capsule pressurizing mode, a needle carrier supporting a fluid delivery needle, the needle carrier and the fluid capsule receiver configured to cause the needle to extend into the fluid capsule pressurizing zone to pierce the pressurized fluid capsule in a second fluid capsule piercing mode; and a body containing the fluid capsule receiver and the needle carrier, the fluid capsule receiver and the needle carrier configured to move along the body to expose a fluid delivery end of the needle in a third fluid delivery mode.

96. A dispenser as defined in any of the preceding or following clauses, wherein the fluid capsule receiver includes a plunger and a fluid capsule carrier, the plunger and fluid capsule carrier having complementary surfaces to locate the fluid capsule therebetween.

97. A dispenser as defined in any of the preceding or following clauses, further comprising a plunger support to support the plunger, at least one interface operable between the plunger support, the fluid capsule carrier, the needle carrier and/or the body to enable displacement of the plunger relative to the fluid capsule carrier in the first, second and/or third modes while exerting a compressive force at substantially consistent magnitude between the plunger support and the body.

98. A method of dispensing a fluid from a fluid capsule, comprising:
   a. locating a fluid capsule on a fluid capsule support surface;
   b. displacing a plunger along an axis to toward engagement with the fluid capsule;
   c. pressurizing the fluid capsule between the plunger and the fluid capsule support surface, so that a membrane of the fluid capsule against the fluid capsule support surface is in a tensioned needle receiving configuration;
   d. displacing the plunger and the fluid capsule support, with the fluid capsule in the needle receiving configuration toward a needle support to cause a capsule-piercing end of a fluid delivery needle thereon, to extend through the fluid capsule support surface to penetrate the membrane to initiate onset of dispensing of fluid through the needle; and
   e. advancing the plunger, the fluid capsule support and the needle support toward a fluid delivery configuration with an opposite fluid delivery end of the needle exposed to penetrate a delivery location.

99. A method of securing a dispensing device following delivery of a fluid therefrom, comprising providing a barrel defining a longitudinal axis terminating at a first fluid delivery end region and a dispenser body movable along the barrel relative to the first fluid delivery end region, the dispenser body movable in a first phase between a pre-dispensing configuration and a dispensed configuration, and in a second phase between the dispensed configuration and a locked post-dispensing configuration, wherein the dispenser body is configured to rotate about the longitudinal axis, at least in part, during the first phase for aligned orientation with at least one locking structure during travel in the second phase.

100. A method of securing a dispensing device following delivery of a fluid therefrom, comprising:
   a. providing a barrel defining a longitudinal axis terminating at a first fluid delivery end region and a dispenser body movable along the barrel relative to the first fluid delivery end region;
   b. displacing the dispenser body in a first phase between a pre-dispensing configuration and a dispensed configuration, and in a second phase between the dispensed configuration and a locked post-dispensing configuration, wherein the dispenser body is rotated about the longitudinal axis, at least in part, during the first phase and/or the second phase for aligned orientation with at least one locking structure during travel in the second phase.

101. A fluid dispenser comprising a barrel defining a longitudinal axis terminating at a first fluid delivery end region; a dispenser body movable along the barrel relative to the first fluid delivery end region in a first phase between a pre-dispensing configuration and a dispensed configuration, and in a second phase between the dispensed configuration and a locked post-dispensing configuration, wherein the dispenser body is configured to rotate about the longitudinal axis during the first phase and/or the second phase for aligned orientation with at least one locking structure configured to lock the dispenser body in the locked post-dispensing configuration during travel in the second phase.

102. A fluid dispenser comprising housing means defining a longitudinal axis terminating at a first fluid delivery end region; dispensing means movable along the housing means relative to the first fluid delivery end region in a first phase between a pre-dispensing configuration and a dispensed configuration, and in a second phase between the dispensed configuration and a locked post-dispensing configuration, wherein the dispensing means is configured to rotate about the longitudinal axis during the first phase for aligned orientation with at least one locking means during travel in the second phase.

103. A fluid dispenser comprising housing means defining a longitudinal axis terminating at a first fluid delivery end region; dispensing means movable along the housing means relative to the first fluid delivery end region in a first phase between a pre-dispensing configuration and a dispensed configuration, and in a second phase between the dispensed configuration and a locked post-dispensing configuration, wherein the dispensing means is configured to rotate about the longitudinal axis during the first phase and/or the second phase for aligned orientation with at least one locking means during travel in the second phase.

104. A dispenser as defined in any of the preceding or following clauses, wherein the dispensing means includes a needle support means with a second fluid delivery end region defined thereon.

105. A dispenser as defined in any one of the preceding or following clauses, wherein the dispensing means includes fluid capsule carrier means movable relative to the needle support means in at least part of the first phase to dispense fluid from a carried capsule therein.

106. A dispenser as defined in any one of the preceding or following clauses, wherein the dispensing means includes plunger means movable relative to the fluid capsule carrier means in at least part of the first phase to pressurize a carried capsule therein.

107. A dispenser as defined in any of the preceding or following clauses, wherein the needle support means is retracted to within the housing means in the locked post-dispensing configuration.
108. A dispenser as defined in any of the preceding or following clauses, wherein the fluid capsule carrier means is configured, during at least part of the first phase, to travel with the plunger means.
109. A dispenser as defined in any of the preceding or following clauses wherein, during at least part of the first phase, the fluid capsule carrier means is configured to rotate axially between lock-unaligned and lock-aligned angular positions.
110. A dispenser as defined in any of the preceding or following clauses, further comprising at least one rotation means provided between the fluid capsule carrier means and at least one of the plunger means and the needle support means.
111. A dispenser as defined in any of the preceding or following clauses, wherein the at least one rotation means includes a first rotation means provided between the fluid capsule carrying means and plunger means.
112. A dispenser as defined in any of the preceding or following clauses, wherein the at least one rotation means includes a second rotation means provided between the fluid capsule carrier means and the needle support means.
113. A dispenser as defined in any of the preceding or following clauses, wherein the capsule carrier means is configured to receive a fluid capsule to be pressurized therein by the plunger means, the fluid capsule carrier means is configured in a first dispensing position to receive an upstream end of a needle on the needle support means to penetrate the fluid capsule as pressurized, and the plunger means is configured to travel with the fluid capsule carrier means toward a dispensed position to express the fluid through the needle at the first delivery end region.
114. A dispenser as defined in any of the preceding or following clauses, wherein the first phase includes at least in part:
   a. a first rotation phase during which the fluid capsule carrier means is rotatable relative to the needle carrier means about the longitudinal axis, as the plunger means approaches the fluid capsule carrier means; and
   b. a second dispensing phase during which the plunger means is movable axially relative to the fluid capsule carrier means toward the dispensed position to pressurize the capsule and dispense the fluid.
115. A dispenser as defined in any of the preceding or following claims, wherein during the second dispensing phase, at least in part, the plunger means is movable axially with the fluid capsule carrying means, toward piercing contact with a needle means on the needle carrier means, to dispense the fluid.
116. A dispenser as defined in any of the preceding or following clauses, wherein the at least one locking means is configured to fix the fluid capsule carrier means at a locking location when the fluid capsule carrier means is in the lock-aligned angular position, the needle support means being biased to travel from the dispensed position toward the locking location.
117. A dispenser as defined in any of the preceding or following clauses, wherein the at least one locking means is configured between the fluid capsule carrier means and the housing means to engage when the dispensing means is in the lock-aligned angular position.
118. A dispenser as defined in any of the preceding or following clauses, wherein the bias is provided by at least one biasing means acting between the first and second fluid delivery end regions.
119. A dispenser as defined in any of the preceding or following clauses, further comprising latch means which configured to release the dispensing means at a transition region following relative travel of the dispensing means along the longitudinal axis, toward and beyond the transition, thereby to release the plunger means.
120. A method as shown or described herein.
121. A dispenser as shown or described herein.

The present disclosure describes what are considered to be practical exemplary embodiments. It is recognized, however, that departures may be made within the scope of the invention and that obvious modifications will occur to a person skilled in the art. Further, the subject matter of the present disclosure supports and provides sufficient basis for any element, feature, structure, function, and/or step of any aspect, and/or exemplary embodiment described in the present disclosure including the figures, clauses and/or claims herein to be combined with any other one or more elements, features, structures, functions, and/or steps of any aspect and/or exemplary embodiment described in the present disclosure including the figures, clauses and/or claims herein, as basis for an independent or dependent claim herein. With respect to the above description, it is to be realized that the dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes may readily occur to those skilled in the art, it is not desired to limit the invention to the exact construction and operation shown and described, and accordingly, all suitable modifications and equivalents may be resorted to, falling within the scope of the invention.

While a device or assembly and an accompanying method have been described for what are presently considered the exemplary embodiments, the invention is not so limited. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

The invention claimed is:

1. A fluid dispenser comprising a barrel defining a longitudinal axis terminating at a first fluid delivery end region; a dispenser body movable in a first phase along the barrel relative to the first fluid delivery end region between a pre-dispensing configuration and a dispensed configuration, and in a second phase along the barrel relative to the first fluid delivery end region between the dispensed configuration and a locked post-dispensing configuration, wherein the dispenser body is configured to rotate about the longitudinal axis during the first phase for aligned orientation with at least one locking structure configured to lock the dispenser body in the locked post-dispensing configuration during travel in the second phase, wherein the dispenser body includes a needle carrier with a second fluid delivery end region defined thereon, the dispenser body includes a fluid capsule carrier moveable relative to the needle carrier in the first phase to dispense fluid from a fluid capsule on the fluid capsule carrier, wherein the dispenser body includes a plunger structure movable relative to the fluid capsule carrier in at least part of the first phase to pressurize the fluid capsule; and at least one rotation interface defined across a plurality of cooperating elements respectively on the fluid capsule carrier and at least one of the plunger structure and the needle carrier, to enable axial rotation of the fluid capsule carrier relative to the barrel, wherein the at least one rotation interface includes a first rotation interface provided between the fluid capsule carrier and the plunger structure and/or wherein the at least one rotation interface includes a second rotation interface provided between the fluid capsule carrier and the needle carrier.

2. A fluid dispenser as defined in claim 1, wherein the fluid capsule carrier is configured to receive the fluid capsule to be pressurized therein by the plunger structure, the fluid capsule carrier is configured in a first dispensing position to receive an upstream end of a needle on the needle carrier to penetrate the fluid capsule as pressurized, and the plunger structure is configured to travel with the fluid capsule carrier toward a dispensed position to express the fluid through the needle at the first delivery end region.

3. A fluid dispenser as defined in claim 2, wherein, during at least part of the first phase, the fluid capsule carrier is configured to rotate axially between lock-unaligned and lock-aligned angular positions.

4. A fluid dispenser as defined in claim 1, wherein the fluid capsule carrier includes a capsule carrier body comprising an open end region opposite the second fluid delivery end region to receive the plunger structure therethrough.

5. A fluid dispenser as defined in claim 4, wherein at least one first guide path is operatively oriented near the open end region to engage a first follower on the plunger structure and/or wherein at least one second guide path is operatively oriented near the second fluid delivery end region to engage a second follower on the needle carrier; or wherein the capsule carrier body is cylindrical and includes a pair of first guide paths and a pair of second guide paths, each pair being symmetrically arranged relative to the longitudinal axis.

6. A fluid dispenser as defined in claim 2, wherein the fluid capsule carrier includes a transverse fluid capsule receiving surface, and a needle passage extending therethrough to receive an upstream end of the needle.

7. A fluid dispenser as defined in claim 6, wherein the plunger structure includes a plunger end region (34a) to travel during at least part of the first phase toward the transverse fluid capsule receiving surface to pressurize the fluid capsule, thereby to express the fluid through the needle.

8. A fluid dispenser as defined in claim 7, wherein the first phase includes at least in part:
   a. a first rotation phase during which the fluid capsule carrier is rotatable relative to the needle carrier about the longitudinal axis, as the plunger end region approaches the transverse fluid capsule receiving surface; and
   b. a second dispensing phase during which the plunger end region is movable axially relative to the transverse fluid capsule receiving surface, at least in part, to pressurize the fluid capsule.

9. A fluid dispenser as defined in claim 3, wherein the plunger structure includes a plunger and a plunger support, the plunger being configured to swivel through at least a predetermined range relative to the plunger support to rotate with the fluid capsule carrier and/or wherein the fluid capsule carrier and the plunger are configured to fix an angular position of the plunger relative to the fluid capsule carrier at least during the first phase.

10. A fluid dispenser, comprising a fluid capsule receiver configured to form a fluid capsule pressuring zone in a first capsule pressurizing mode, a needle carrier supporting a fluid delivery needle, the needle carrier and the fluid capsule receiver configured to cause the needle to extend into the fluid capsule pressurizing zone to pierce the pressurized fluid capsule in a second fluid capsule piercing mode; and a body containing the fluid capsule receiver and the needle carrier, the fluid capsule receiver and the needle carrier configured to move along the body to expose a fluid delivery end of the needle (26) in a third fluid delivery mode.

11. A dispenser as defined in claim 10, wherein the fluid capsule receiver includes a plunger and a fluid capsule carrier, the plunger and fluid capsule carrier having complementary surfaces to locate the fluid capsule therebetween.

12. A dispenser as defined in claim 11, further comprising a plunger support to support the plunger, at least one interface operable between the plunger support, the fluid capsule carrier, the needle carrier and/or the body to enable displacement of the plunger relative to the fluid capsule carrier in the first, second and/or third modes while exerting a compressive force at substantially consistent magnitude between the plunger support and the body.

* * * * *